United States Patent [19]

Barrett et al.

[11] 4,063,097

[45] Dec. 13, 1977

[54] X-RAY BODY SCANNER FOR COMPUTERIZED TOMOGRAPHY COMPRISING INNER FLUID CONTAINER SURROUNDED BY OUTER FLUID CONTAINER

[75] Inventors: David M. Barrett, Brookfield, Wis.; John L. Henkes, Jr., Latham, N.Y.; Lewis S. Edelheit, Schenectady, N.Y.; Robert Godbarsen, Elm Grove, Wis.

[73] Assignee: General Electric Company, Schenectady, N.Y.

[21] Appl. No.: 723,777

[22] Filed: Sept. 16, 1976

[51] Int. Cl.² .......................... A61B 6/02; A61B 6/04; G03B 41/16
[52] U.S. Cl. ................................. 250/360; 250/445 T
[58] Field of Search .................. 250/444, 445 T, 451, 250/360

[56] References Cited

U.S. PATENT DOCUMENTS

| | | | |
|---|---|---|---|
| 3,867,634 | 2/1975 | Hounsfield | 250/360 |
| 3,881,110 | 4/1975 | Hounsfield | 250/360 |
| 3,973,126 | 8/1976 | Redington et al. | 250/445 T |

Primary Examiner—Archie R. Borchelt
Assistant Examiner—T. N. Grigsby
Attorney, Agent, or Firm—Ralph G. Hohenfeldt

[57] ABSTRACT

An x-ray source, whose output is collimated into a thin fan-shaped beam, and detector means spaced from the source are mounted for scanning and orbiting jointly about a body in a partial or complete revolution to provide x-ray intensity data for reconstructing an image. The detector and source combination and the body are moved relative to each other in an axial direction for scanning the body layers in sequence. In one embodiment the x-ray source is pulsed as it scans and in another the fan-shaped beam is on continuously and readout is done sequentially so in either case a large number of intensities for each layer are obtained. A high precision encoder system is used to synchronize x-ray pulses and readouts spatially and with line frequency. Means are provided for storing the cables which lead to the rotatable source, and the detectors and other moveable components. An embodiment for scanning a body part such as a breast has means for conditioning and controlling water in which the part is immersed.

15 Claims, 23 Drawing Figures

X-RAY BODY SCANNER FOR COMPUTERIZED TOMOGRAPHY COMPRISING INNER FLUID CONTAINER SURROUNDED BY OUTER FLUID CONTAINER

BACKGROUND OF THE INVENTION

This invention relates to apparatus for examining the human body with penetrating radiation such as x-ray and gamma radiation. Although novel features, discussed in detail hereinafter, are applicable to apparatus for examining the entire body or parts thereof such as the torso, for convenience, the novel features will be described primarily in reference to apparatus for examining human breasts.

The basic features of one type of examination apparatus in which the invention may be employed are illustrated in co-pending U.S. Pat. application Ser. No. 600,874, now Pat. No. 3,973,126 filed July 31, 1975, now U.S. Pat. No. 3,973,126 assigned to the assignee of this application. The disclosure of said application is incorporated herein by reference. Background information on the state of the art may be obtained from an article entitled "Image Reconstruction From Projections" by R. Gordon, G. T. Herman and S. A. Johnson in Scientific American, October, 1975, Vol. 233, No. 4, p. 56.

Detection of breast tumors is a process which depends on being able to differentiate radiation absorption by normal tissue and absorption by the tumor or other malignancy which has substantially equal density. Heretofore, radiographic films, fluoroscopic screens and xeroradiographic plates were used as the x-ray detecting devices but none of these devices had sufficient sensitivity to differentiate between normal and abnormal tissue.

Recently developed procedures for soft tissue differentiation with x-rays, using a scanning method, are described in U.S. Pat. Nos. 3,778,614, 3,867,634 and 3,881,110. As described in the patents, one or more finely collimated gamma ray or x-ray beams from a common source are directed through the examination subject and to a detector array on the side opposite of the subject from the source. In one scheme, the source and detector are translated back and forth and at the end of each translation the source and detector are incremented rotationally. Signals corresponding with detected density variations are fed into a computer which, when information from the whole scan is complete, produces data representative of density variations in the transverse plane. The data may be used to control a suitable display device such as a picture tube which enables visualization of the reconstructed image. The procedure is a variation of what is commonly called tomography.

Calculations of the image representative data is simplified if, as in accordance with some of the prior patents, the skin-to-air interface and density variations across the scanning beam are reduced by surrounding the body part in a fluid having a density or x-ray transmissibility substantially equal to that of tissue. Water meets this requirement substantially as mentioned in above cited U.S. Pat. No. 3,881,110. On the other hand, in prior art computerized tomography apparatus for examining portions of the body other than breasts and when examining such portions with apparatus using the new features and principles of body scanning with radiation disclosed herein, surrounding the examination subject with water is not always feasible but computerized image reconstruction is still obtainable if proper allowances are made. Heretofore, x-ray scanning apparatus had not achieved the levels of image definition and examination speed for practical mass screening of female breasts nor was there any apparatus available that was dedicated to making breast examinations or examinations of other body portions by scanning techniques that gave the subject x-ray dosages closer to the lower dosages which are theoretically obtainable.

SUMMARY OF THE INVENTION

In the illustrative breast scanner herein described, a woman whose breasts are to be examined is supported substantially horizontally in a position where one breast at a time hangs vertically into a fluid filled x-ray transparent container. The x-ray source and detector means are mounted on a scan arm or rotor as it is herein called for convenience, rotates about a vertical axis substantially coincident with the apex of the breast such that the source on one side and the detector on the other side of the breast orbit together.

The rotor is mounted for rotation on an elevator. The rotor and elevator are subject to azimuth and elevation control, respectively. They can be positioned manually for the purposes of servicing the apparatus and for setting up a subject for an examination. The rotor azimuth and elevator drives are programmed during an examination and the x-ray source is preferably pulsed at regular intervals to, in effect, stop motion as the source and detector orbit about the breast or other body portion that is being examined. After each scanning revolution of the rotor which is preferably 360° but may be 180°, the elevator is incremented axially such as in steps typically of centimeter or a half-centimeter along the axis of rotation. After each scan the rotor rotates oppositely from the preceding scan. These alternately opposite scans are repeated until the entire height of the breast is scanned in successive layers.

The x-ray beam is collimated into a thin layer which, for example, may be about one centimeter thick. It is also fan-shaped as it emanates from substantially a point source and it subtends the body portion such as the breast and the fluid around it. The most divergent end of the beam falls on an array of x-ray detector elements. The signals from the detector elements are delivered to computer storage between each x-ray pulse.

In the breast scanner embodiment which is herein described, the breast, as indicated above, is in an inner fluid filled container which is stationary during an examination so the fluid therein does not experience any undesirable turbulence that would move the breast undesirably. This inner container is preferably surrounded by a larger outer container which is also filled with fluid such as water during an examination. The inner and outer containers are always maintained at a constant height. The outer container rotates or angulates synchronously with the x-ray source and detector but the outer container remains at a constant elevation in the described embodiment. The outer container is filled with water and shaped so that x-ray absorption across the fan-shaped beam is as close as possible to being constant. The inner container is open at the top to permit water to overflow and thus assure that there is water contiguous with the topmost layer of the breast and its adjacent tissue.

OBJECTS

A general object of this invention is to provide x-ray body layer scanning apparatus for computerized tomography which yields more information than prior apparatus with reduced x-ray dosage.

Another general object is to provide x-ray scanning apparatus which enables examination of patients in shorter periods.

Other objects are:

to provide for using a thin diverging or fan shaped x-ray beam to scan successive layers of the body;

to provide for pulsing the x-ray source and, hence, the beam, as the beam rotates so that x-ray intensity data can be read out similarly to motion being stopped;

to provide for preserving the benefits of using a fan-shaped beam, even though it is on continuously while it is rotated, by providing for reading out instantaneous x-ray intensity signals alternately and sequentially;

to provide an encoder for producing clock signals that can be used for controlling and timing a variety of interrelated system functions;

to provide, more specifically, for using encoder clock pulse signals to sense angular acceleration of the beam prior to x-ray pulse initiation and to prevent x-ray from turning on if azimuth angular velocity is improper;

to provide an encoder system for enabling a computer that is programmed for image reconstruction to associate each bit of x-ray information with a contemporaneous scanner rotation azimuth angle and body layer so that execution of the programmed algorithm will result in data for developing a true image having high resolution and contrast;

to provide for using the encoder clock system to set precisely the azimuth angles at which x-ray pulses are produced and read out, and to control the x-ray pulses so they are centered or symmetrical about reproducible azimuth angle points regardless of x-ray pulse duration;

to provide an encoder clock system which enables temporal and spatial synchronization of functions with stable power line frequency;

to use the encoder clock signals for controlling the length or duration of x-ray pulses as required for desired x-ray exposures and for extending and shortening x-ray pulses symmetrically about equiangularily spaced apart angular points in a scanned layer so that the center points of the x-ray pulses in any layer are maintained in congruency with the center points of corresponding pulses in other layers for either direction of rotation, one advantage of this object being that the computer image reconstruction algorithm may be simplified in comparison with a case where the x-ray pulses are extended in one angular direction;

to use the encoder clock for determining the time between x-ray pulses, or if the source is not pulsed, to determine the time between acquisition of discrete x-ray intensity signals, which are detected sequentially and readout alternately, at which the signals can be readout;

to provide an encoder clock system which enables timing and otherwise controlling a system as mentioned above where multiple x-ray sources and a corresponding number of detectors are employed for the purpose of further reducing the time required for scanning a body layer;

to provide in body scanning apparatus wherein the x-ray source and the detector are on a scan arm, herein called a rotor, and the rotor is on an elevator or other translator, a take-up mechanism for handling the many cables that lead to the x-ray source, detectors and data acquisition components which are mounted on the rotor in such manner as to accommodate distance changes resulting from rotation and translation;

to provide a cable take-up mechanism which stores the cables in a small space, isolates them from becoming entangled in other mechanism and with theirselves, minimizes impediment of rotor rotation and translation by the cables, prevents the cables from being overstressed by bending and which is designed to handle stiff cables, soft flexible cables, tubes and other elongated elements in x-ray scanning apparatus and other apparatus too;

to provide for surrounding a patient or a part thereof in water and containing the water in such fashion that the x-ray beam will encounter substantially uniform absorption across its width;

to provide for maintaining the container, in which parts of a patient undergoing x-ray scanning examination are disposed, stationary during the examination so that the water turbulence and movement of the body part are avoided;

to provide for conditioning temperature and other qualities of the water for maximum patient comfort and for assuring the integrity of the x-ray intensity data;

to provide means for programming conditioning and handling the water such that each x-ray examination may be conducted in the shortest time;

to provide for filling the water container at a fast rate until there is only about enough volume remaining for the patient and some additional water to thereby avoid splashing and then filling at a slower rate and finally causing moderate overflow to assure that the water contacts the patient at the open top of the container and to assure that conditioned water is not used excessively, and to introduce water flow from the bottom of the container for flow in the direction of overflow so that turbulence and possible entrapment of bubbles will be avoided.

How the foregoing and other more specific objects of the invention are achieved will appear in the following more detailed description of an illustrative embodiment of the invention given in conjunction with the drawings.

DESCRIPTION OF A PREFERRED EMBODIMENT

Figure 2:
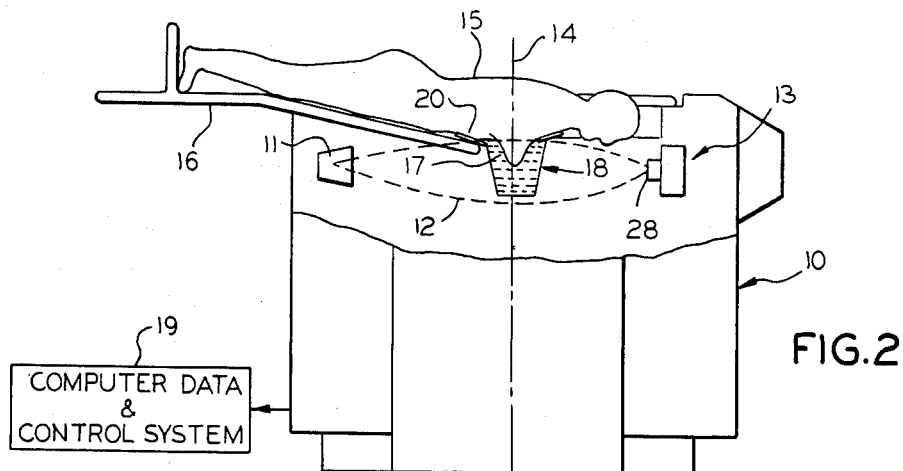
FIG. 2 is a schematic diagram showing how the patient is disposed relative to the apparatus in a breast scanning embodiment thereof.

Attention is invited to FIG. 2 which shows in schematic form breast scanner apparatus in which the improvements that are generally applicable to body scanners discussed herein may be incorporated. The illustrative breast scanner apparatus comprises a housing 10. Within the housing is a source 11 of penetrating radiation such as x-ray or gamma radiation. Diametrically opposite of the source on a circle of revolution 12 is a multi-element radiation detector assembly 13. As will be explained, the radiation source 11 and detector are mounted on a scan arm or rotor which rotates about an axis 14 that is preferably substantially coincident with the center of the image field. The source 11 and detector 13 are not necessarily at the same radius from the axis of revolution. In the FIG. 2 embodiment, the axis of rotation is vertical as it is in the illustrative breast scanner version of the apparatus. In versions that are not specialized for scanning breasts, but are adapted for examining and scanning other parts of the body or the whole body, the rotational axis may be horizontal or at some angle.

In the FIG. 2 embodiment, the breast examination subject 15 is brought to a face down position with a tilting frame 16 which is described in co-pending application Ser. No. 600,874, filed July 31, 1975, and assigned to the assignee of this application. Said application is incorporated herein by reference. In FIG. 2 one of the breasts 17 at a time is disposed in a water container assembly 18 for examination purposes. The body around the breast is supported on an apertured surface 20 which is shown fragmentarily.

In the breast examining and whole body scanning versions of the apparatus the x-ray beam emanating from a small spot in source 11 is formed into a relatively thin fan-shaped beam which diverges horizontally toward detector 13 sufficiently to include all parts of the body being examined. In the breast scanner version which is described and also illustrated herein, the beam also passes through the water in containers 21 and 22 which comprise container assembly 18. The fan-shaped beam is preferably thin in the direction of the rotor's rotational axis. Typically, the beam may be one centimeter thick or somewhat more or less. The source 11 and detector 13 orbit the body jointly to record the images taken in a single plane and then the rotor having the source and detector on it is incremented downwardly and rotor rotation is reversed for the next scan. During each 360° rotational scan, the electric signals corresponding with x-ray image intensities for increments through which the beam passes at different angles in the scan are read out from multi-element detector assembly 13 and stored in a computer 19 in which they are processed for display.

Figure 1:
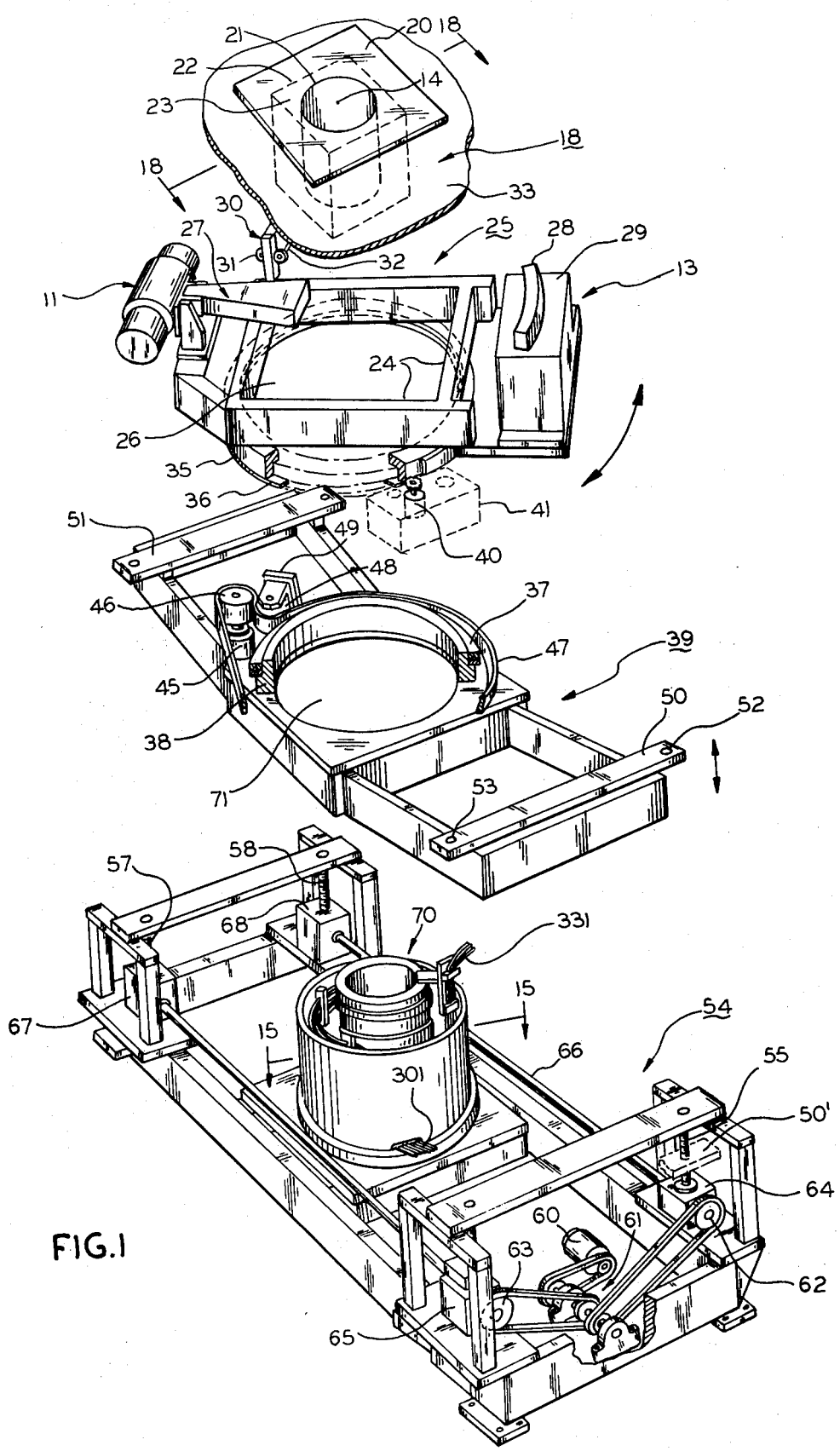
FIG. 1 is an exploded schematic view of the principal mechanical components of the x-ray scanning apparatus.

The principal mechanical components of the apparatus will now be outlined in reference to FIG. 1. The mechanism to be described is for a specialized breast scanner but the scanning and x-ray pulse timing concepts which are elucidated are applicable to whole body scanning apparatus too as will be appreciated by those skilled in the art.

In FIG. 1 diagrammatic exploded view, the breast of the patent to be examined is disposed in an inner container 21 which is filled with fluid such as water and is stationary during a scanning operation. Hence, the water is stationary and so is the breast as is necessary to obtain valid x-ray intensity data. Inner container 21 is shown as being cylindrical in FIG. 1 but it may be conical or vertically tapered to conform more closely with the breast. The selected fluid is for producing x-ray intensities which are substantially uniform across the field of the detectors and substantially equal to those of soft tissue so as to always fall within the dynamic sensitivity range of the x-ray detector. The fluid may, for example, comprise water which may contain dissolved surfactants, germicides and fungicides to minimize bubble formation and foaming within inner container 21 and to assure wetting and prevent growth of microorganisms.

Container 21 is surrounded by an outer container 22 that defines a surrounding space 23 which is also occupied preferably by the same fluid during an examination. Outer container 22 rotates with the rotor on which the x-ray source 11 and detector 13 are supported during an examination but the outer container does not translate axially along the vertical rotational axis 14. Part of the structure on which part of the patient's body surrounding the breast is supported is marked 20.

The rotor structure or scan arm as it is sometimes called is designated generally by reference numeral 25 and comprises a frame 24 which defines a central open space 26. The x-ray source 11, comprising a casing and an x-ray tube therein, not visible, is mounted on one side of the rotor 25. The x-ray source has a collimator 27 for defining the thin fan-shaped diverging x-ray beam discussed above. An arcuately arranged array of x-ray detectors which are collectively marked 28 are located on the frame diametrically opposite from the x-ray source and in the plane of the beam. The detector array 28 is mounted on a box 29 in which there are electronic devices, not visible, that facilitate storing and multiplexing the electric signals, developed by the detectors coincident with the x-ray pulses during the scan, to the computer 19 for processing. A suitable x-ray multi-element detector 28 is illustrated in co-pending application Ser. No 616,930, filed Sept. 26, 1975, and assigned to the assignee of this application.

In the computerized image reconstruction system, described herein, a spatial distribution of x-ray intensities must be translated into electric signals by the detector 28 such that the signals can be processed by means of a suitable computer algorithm to yield a composite image. In this embodiment, the x-ray source is pulsed to produce a train of pulses at regularly spaced angles of rotation during a scan by the rotor and all of the detector elements are exposed. The time between pulses is used to readout the detector elements. The encoder system, to be described later, controls the x-ray pulse sequencing. As an alternative, not shown, to repeatedly pulsing and rotating through a small angle, the encoder system may also be used to control rotation in such manner that the rotor supporting the x-ray tube and detectors will repetitively step through a small angle and come to a stop during which time the source may be pulsed. Those versed in the art to which the invention pertains will appreciate that where the fan-shaped beam is rotated and not translated, when scanning the body layers in sequence as is the case in the exemplified embodiment, pulsing of the x-ray beam may be avoided if suitable measures are taken. An alternative system which does not pulse the x-ray source but still employs the fan-shaped x-ray beam will be described later in reference to FIG. 20.

In FIG. 1 the means for driving outer water container 22 rotationally without displacing it axially are shown symbolically as comprising a post 30 fastened to scanner or rotor 25 and a pair of rollers 31 which are on arms 32. The arms are joined with a member 33 to which the outer container 22 is fastened. Thus, when rotor 25 is moved up and down in connection with scanning, rollers 31 can follow the surface of post 30 and the post will drive the outer container 22 rotationally at any elevation of the rotor 25. Thus, it is evident that inner water filled container 21 will not rotate but outer water filled container 22 will be driven rotationally and both containers will always stay at the same constant height.

In this embodiment, the bottom of rotor 25 has a ring 35 fastened to it. The ring also has a concentric ring gear 36 having its teeth outwardly presented. Ring 35 and its associated gear 36 rest on and are fastened to a bearing 37 carried on an annular member 38 which is mounted on an axially translatable frame or elevator identified generally by the number 39. Mounting of the rotor 25 on bearing 37 permits the rotor to rotate through 360° and more in alternately opposite directions as is required during the scanning procedure. With the rotor 25 thus supported on elevator 39, the rotor can be raised and lowered incrementally by moving the elevator incrementally after each scan. Ring gear 36 is used to drive an encoder 40 which is in a box 41, shown in dashed lines, along with some other electrical components which will be discussed later.

Mounted on the elevator 39 is a servomotor 45 for driving rotor 25 rotationally or in azimuth. The motor shaft has a pulley 46. The pulley drives a belt 47, shown fragmentarily. The belt runs on the periphery of ring 35 which is fastened to the bottom of rotor 25 as is possible where in the actual assembly the ring 35 is in place on bearing 37. The belt is tensioned by an idler pully 48 which is on a bracket 49 that is fastened to elevator 39. In this schematic representation of the mechanism, the elevator has two cross bars 50 and 51. Each cross bar has a pair of bushed and internally threaded holes 52 and 53 which are for accommodating power driven lead screws that drive the elevator 39 and, of course, rotor 25 down in steps as is required during a scanning procedure.

For the sake of showing how the elevator 39 is assembled to a base structure 54 to enable supporting and driving the elevator, one of the bars 50, marked 50' is shown fragmentarily in the base structure 54 with one of four lead screws 55–58 threaded through it. It will be evident that when the lead screws which are coupled in tandem are driven rotationally the elevator 39 will move up or down depending upon the direction of rotation of the lead screws.

The lead screws are driven by a servomotor 60 through a belt and pulley system 61. The belt drives some shafts 62 and 63 in gear boxes 64 and 65 in which the lead screws are mounted and driven. These gear boxes are conventional and their function should be evident to those skilled in the art. Cross shafts 66 and 67 couple gear boxes 64 and 65 with another pair of gear boxes 67 and 68 which drive lead screws 57 and 58. Mounted inside of the base frame 54 on a boxlike structure 69 is a new type of cable take-up device which is generally designated by the number 70 and which will be described in detail hereinafter.

When the apparatus in FIG. 1 is actually assembled, as opposed to it being in exploded form as shown, the elevator 39 is carried on the lead screws in base structure 54 and the rotor 25 is journalled on the elevator. The elevator 39 has a central opening 71 to accommodate the cable take-up device 70 within it. The water filled containers 21 and 22 are, of course, disposed in the path of the fan-shaped x-ray beam between source 11 and detector array 28.

Figure 3:
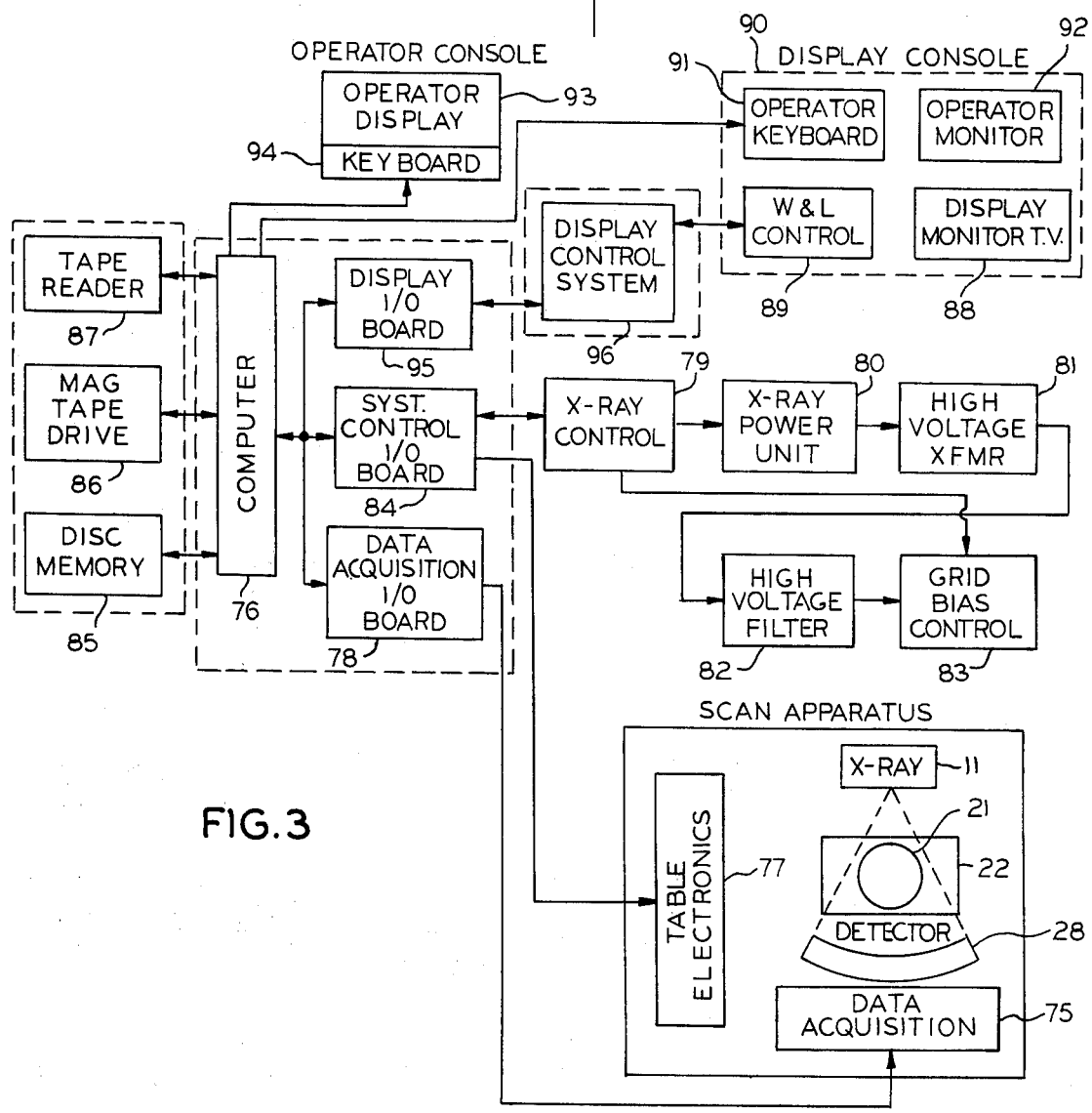
FIG. 3 is a block diagram of the data gathering and control components of the x-ray scanning system.

Before proceeding with a detailed description of the specific improvements, an overview of the entire system will be taken in reference to FIG. 3 primarily. Basically, the system involves projecting a beam of x-radiation through a layer of the examination subject and letting the rays that pass through the subject fall on an array of detectors. The x-ray source and detectors are orbited jointly around the examination subject and the source is pulsed at predetermined intervals such that the detectors produce a sequence of electric signals that are related to the absorption of all volume increments in the layer. A similar scan is made of each layer. The absorption data is digitized and usually stored in a memory associated with a computer. The computer is controlled by a suitable program that executes an algorithm which processes the data in such manner that digital numbers can be made to represent absorption coefficients, for each pixel (picture element) within any selected layer. This permits reconstruction and display of the image which has been scanned. It is necessary, of course, to relate each absorption coefficient raw data word with the scan angle and layer in which it is obtained. The rotor or scan arm azimuth angles at which absorption measurements are initiated and terminated in a scan must be precisely determined. The azimuth angles of the rotor must be known at all times.

In the body scanner, particularly the specialized breast scanner described herein, the scanner may be considered to be at zero degree azimuth when the x-ray source 11 and the detectors 28 are in line and parallel with the paper in FIG. 2 with zero at the foot end of the subject. As viewed from the top of FIG. 2, clockwise azimuth angles are considered positive and counterclockwise angles are considered negative. In accordance with the present invention, the x-ray source is pulsed during the time that the scan arm rotates 360° preferably.

A convention has been adopted for specifying the azimuth or rotational angles of the scan arm which is herein otherwise called the rotor 25. When the subject is positioned as in FIG. 2, zero azimuth for the x-ray source is at the foot end of the patient on a line between her feet and extending toward the head. The head is at 180° azimuth in this FIGURE. When the patient is loaded onto the apparatus, the rotor and specifically, the x-ray tube is positioned at 90° azimuth or a quarter of a revolution beyond 0° azimuth considering that the x-ray source has been positioned clockwise from 0° as viewed from above the patient. Since the patient and apparatus are made ready with the x-ray source at about 90° of clockwise rotation and since the first scan is intended to go clockwise the rotor is not taken back to zero azimuth counterclockwise at the start but it is caused to start clockwise at 90° azimuth. The clockwise angle between 90° and exactly 135° azimuth is allowed for the rotor to accelerate and achieve constant angular velocity. At exactly 135° x-ray pulsing is initiated. This azimuth angle of 135° is the zero degree point for x-ray pulsing and if 360° of rotor rotation is added it is also the turn-off or 360° point where x-ray pulsing is terminated for the body layer that has been scanned. Hereafter, in this description, for the sake of simplicity, x-ray 0° will be used to indicate the azimuth at which x-ray pulsing beings and x-ray 360°, which is actually coincident with zero will be used to indicate the angle at which x-ray pulsing is terminated.

In the clockwise scan just discussed, the true azimuth, referenced to zero degrees at the foot end, of the x-ray source when pulsing terminates is 135° plus 360° which equals 495°. After that the rotor can coast another 45° and if it does not stop earlier it is braked at 540°.

A counterclockwise scan is initiated from true azimuth of about 540° or less and again 45° or less is allowed for the rotor and x-ray source to accelerate and attain constant velocity which it has at true azimuth of exactly 495° where x-ray pulsing is initiated for counterclockwise scans. This 495° true azimuth coincides with true azimuth of 135° at which x-ray pulsing starts for clockwise rotation and can again be considered x-ray 0°. X-ray pulsing for a counterclockwise scan terminates at exactly a true azimuth of 495° minus 360° or 135° and the rotor again coasts up to 45° and reaches 90° true azimuth which is where the preceding clockwise scan started from and the next one will start from.

By way of example and without limitation, in one embodiment the x-ray source is pulsed on every 3.6° of rotation in every layer. The pulse envelope endures for about 0.5° or 4.4 milliseconds. Within each x-ray pulse envelope four encoder pulses at 1.1 millisecond intervals occur. Between x-ray pulses, about 100 milliseconds are available for reading out the detectors. There are about 128 detector elements, in this example, in the array of detectors 28.

The scanner rotor 25 is driven at 6 rpm, in this example, which permits a 360° scan of a body layer to be completed in 10 seconds or 180° in 5 seconds if a half revolution is used. Each layer is one centimeter thick but taking thinner layers is contemplated. The maximum size of a breast is usually about 15 centimeters so it can be examined in a total of about 150 seconds of actual scanning time with 10 second scans. Smaller breasts require fewer scans and can be examined in less time. The operator can set the number of layers to be scanned to cover the entire breast and substantially no more. In the version of the scanning apparatus for examining the torso or other major whole body portion, more or fewer layers are scanned at the election of the operator.

The above values, as stated, are only illustrative. For instance, scanning speeds of 6.25 and 12.5 rpm and 4.8 and 9.6 seconds per scan are used in another embodiment. The important aspect is that the pulses are spatially and temporally synchronized with scanning angles and, as will appear, to line frequency. A feature of the present invention is an encoder system, to be described later, which makes this possible with high precision.

In FIG. 3, a block marked table electronics 77 is representative of the circuitry for determining and controlling the scanner angles and selecting the layers. The table electronics are coupled to the computer through a data acquisition input-output board 78.

Means are provided for energizing and controlling the x-ray source 11. The x-ray control block 79 is for establishing the operating parameters of the x-ray tube such as the potential and filament current. These operating parameters must be maintained constant to obtain useful absorption date and for this purpose control 79 controls the x-ray power unit 80 which, in turn, sets the high voltage output of x-ray transformer 81. The applied voltage may be filtered in a filter symbolized by block 82. The block 83 represents a grid bias control for turning on and off the x-ray tube grid biasing potential which starts and stops the x-ray pulses. The x-ray system is interfaced with the computer by means of an input-output board 84.

The required absorption data in digital form is stored in a disc memory 85 for processing in accordance with the computer algorithm. The computer program is stored in a magnetic tape module 86. The tape recorder is marked 87. Digital data representative of an image may be displayed on a soft or hard copy monitor symbolized by the block 88. Means are provided to select a portion of the image having a particular contrast range or gray scale and impart to it a full contrast scale from white to black. Such means are symbolized by the block 89 called the W-L (window and level) control. At the display console 90, the operator is provided with a keyboard 91 for issuing various commands to the display control system 96. The display console could also have the monitor 92 for monitoring the x-ray generator output. On the machine itself, there is an operator console 93 which also has a keyboard 94 for controlling the system. The remote display console is interfaced with the computer with a display input-output board 95 and a display control system 96. Scanning is automatic under computer control after the patient is set up and a start command is initiated by the operator.

An important improvement in the body scanner apparatus herein described is the encoder system. Its primary function is to provide the system controller, which can be the computer or a separate microprocessor, not shown, with pulses as a function of scanner position. These pulses after being processed in the system controller or computer, initiate the x-ray pulse commands as a function of the scanner rotation position and power line frequency. The encoder pulse rate is used by the system controller to determine scanner rotational speed.

Figure 4:
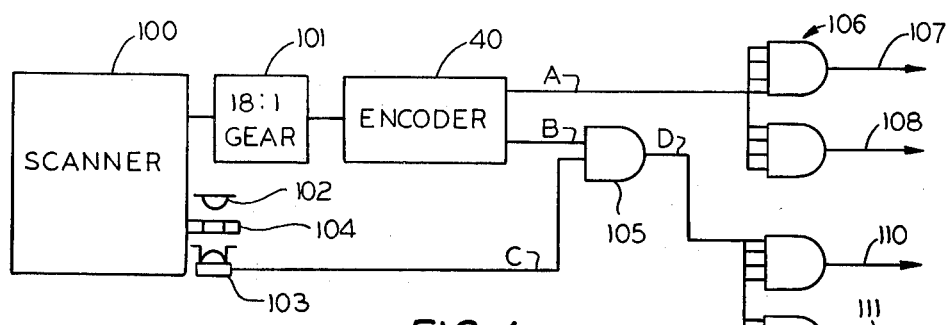
FIG. 4 is a block diagram of part of an encoder system in accordance with the invention.
Figure 5:
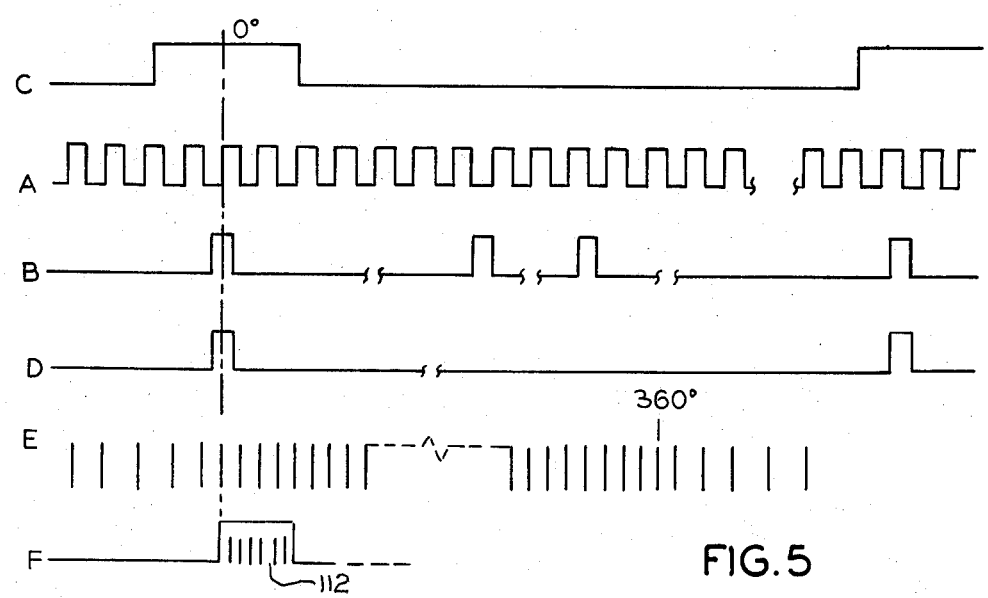
FIG. 5 shows a group of waveforms that are useful for explaining operation of the encoder system.

Refer now to FIGS. 4 and 5 for a description of one embodiment of the encoder system. In FIG. 4, the block marked 100 represents the scanner which comprises the rotor 25 in FIG. 1 on which the x-ray source 11 and detector assembly 13 is mounted. The encoder 40 produces output pulses in response to rotor rotation and is a commercially available type the details of which need not be shown. It may comprise a disc with holes arranged in a circle at equal angles. A light source, such as a light emitting diode, is on one side of the disc and a light sensor on the other side. As the holes pass through the light beam due to encoder shaft rotation, the sensor produces a sequence of electric pulses. By way of example, and not limitation the encoder in an actual embodiment produces 500 pulses per encoder shaft revolution. Since the gear ratio between the encoder and the scanner as symbolized by the block 101 in FIGURE is 18:1, 9,000 output pulses appear on line A for each 360° of scanner rotation. Pulses are produced at a constant rate during scanning because the scanner servomotor speed is held constant. When the scanner is accelerating or decelerating before and after reaching 0° where x-ray pulsing starts and 360° of rotation where x-ray pulsing stops, respectively, encoder pulses are produced at a varying rate.

On output line B, encoder 40 also provides 1 pulse for every encoder shaft revolution or 18 pulses for every full revolution of scanner rotor 25. A third pulse signal appearing on line C is produced independent of the encoder. The rate of pulses on line C is 1 for every 360° scan revolution and this pulse is produced at about the x-ray zero azimuth angle. The pulses on line C are produced independently of the encoder using photoelectric elements comprising a light source 102, a detector 103 and an apertured element 104. The pulse signal C has a 10° aperture.

As can be seen in FIG. 5 where the waveforms are shown, the encoder is phased so that pulse signal B falls within the aperture of pulse signal C. The A series and B series of pulses are necessarily related temporally and spatially because they are generated from the same encoder shaft. The B and C signal pulses are coincident once per scanner revolution and, as can be seen in FIG. 5 where the x-ray zero angle condition is identified by a dashed line, the center of the B pulse coincides with the rise of the first pulse in the A train so as to obtain a precise spatial registration of the zero position to the A pulse train. The output pulse indicating the zero point appears on line D in FIG. 4 and results from the AND function of gate 105 which produces an output signal D upon the coincidence of signals B and C.

The pulse train A is transmitted through an AND gate driver 106 to the system controller. Suitable drivers are National DM 8830 or equivalent. For each pulse in train A, output line 107 of the driver goes high and output line 108 is held low. Zero indicating pulses D resulting from coincidence of pulses B and C are delivered to a driver 109 and to the system controller by way of lines 110 and 111. All lines are isolated electrically at the receiving end, using light-coupled isolators, not shown. The receivers may be Fairchild FDC 820 or equivalent, followed by a Schmitt trigger buffer, type SW 7414, neither of which are shown.

As shown in FIG. 5, the encoder pulses in train A are occurring at a uniform rate. Such will be the case only when the scanner is rotating at a uniform angular speed. The system is such that the first x-ray pulse will be initiated only if scanner rotational speed and, hence, pulse rate is a predetermined constant. Constant scanner angular speed is obtained with the azimuth drive which will be discussed later.

When a layer of the subject's body such as in the breast is to be scanned, assuming the subject is properly set up, the scanner or rotor will start rotating from an angle of about 45° prior to x-ray 0° as that term was defined earlier. This allows the scanner or azimuth drive to accelerate and reach a constant speed when x-ray zero or turn-on position is attained and the first x-ray pulse is initiated. The first x-ray pulse is initiated only if the rotor 25 is at constant predetermined speed when the rotor reaches x-ray 0° for one scan direction and x-ray 360°, which is the same position, for the other scan direction. The scan is automatically aborted if rotor speed is not constant by the time the rotor reaches x-ray 0°.

The encoder is, in any event, putting out a continuous pulse train during rotor acceleration, during the uniform speed interval and during deceleration of the scanner. This is exemplified in pulse train E in FIG. 5 and these pulses are actually those that appear on line A in FIG. 4. It will be evident that to the left of the x-ray zero marker in pulse train E, the pulses have nonuniform and decreasing space between them, indicating acceleration. Just prior to zero, and from zero to just beyond 360° of rotation where x-ray pulses are stopped, the encoder pulses are uniform because of the azimuth drive running at a constant speed. After 360° of rotation or at x-ray-off position, the scanner decelerates and comes to a stop in about 45° under normal conditions. Converse angles apply for the case of reverse rotor rotation. Suitable limit switches and stopping means are provided to limit rotation to no more than 90° in either direction beyond x-ray zero or x-ray 360° for reversed scan revolutions. This will be discussed in greater detail later.

In FIG. 5, the x-ray pulse interval is shown on line F and the first pulse is initiated at x-ray 0° of the scanner or rotor and repeated every 3.6° of rotor and x-ray source rotation in this example as mentioned earlier. Other repetition rates could be used. In this example, as previously mentioned, the pulse duration is 4.4 milliseconds and within that time 4 encoder pulses 112 of 1.1 milliseconds spacing occur. Those skilled in the art will appreciate that the x-ray pulse frequency can be different than the explemary values just given and that this will depend on available x-ray intensity, individual pulse duration, scanning speed, the computer algorithm used for reconstruction of the image and, among other things, the degree of image resolution required. The speed sensing system allows a 5° buffer period for monitoring and determining if the scanner is operating at constant velocity. The x-ray pulses start only if rotor velocity is constant. The scan is aborted automatically if velocity is not constant. If scan velocity is constant, the x-ray can turn on at x-ray 0°. The computer, in performance of its control functions, keeps track of the x-ray pulses and indexes them and causes the high voltage to the x-ray source to turn off at the end of each scan.

A scheme for controlling x-ray exposures which is preferred to the one described in the immediately preceding paragraphs will now be described. In the previous embodiment each x-ray pulse or exposure interval was started when a predetermined number or encoder pulses had been counted. When shorter or longer x-ray pulses were selected to get decreased or increased exposures, the x-ray pulses contracted and expanded on one side of the starting point. In other words, the x-ray pulses were not centered about the angles between pulses. This complicates the algorithm used by the computer to reconstruct the x-ray image.

In the previous scheme, the x-ray pulses were synchronized spatially or angularly but there was no assurance of getting x-ray pulse synchronization with power line frequency. The preferred embodiment accomplishes line frequency synchronization and has the x-ray pulses symmetrical about their spacing angles as determined by the encoder. The centers of all x-ray pulses in all layers of the body will then be congruent regardless of the length of the pulses.

Figure 8:
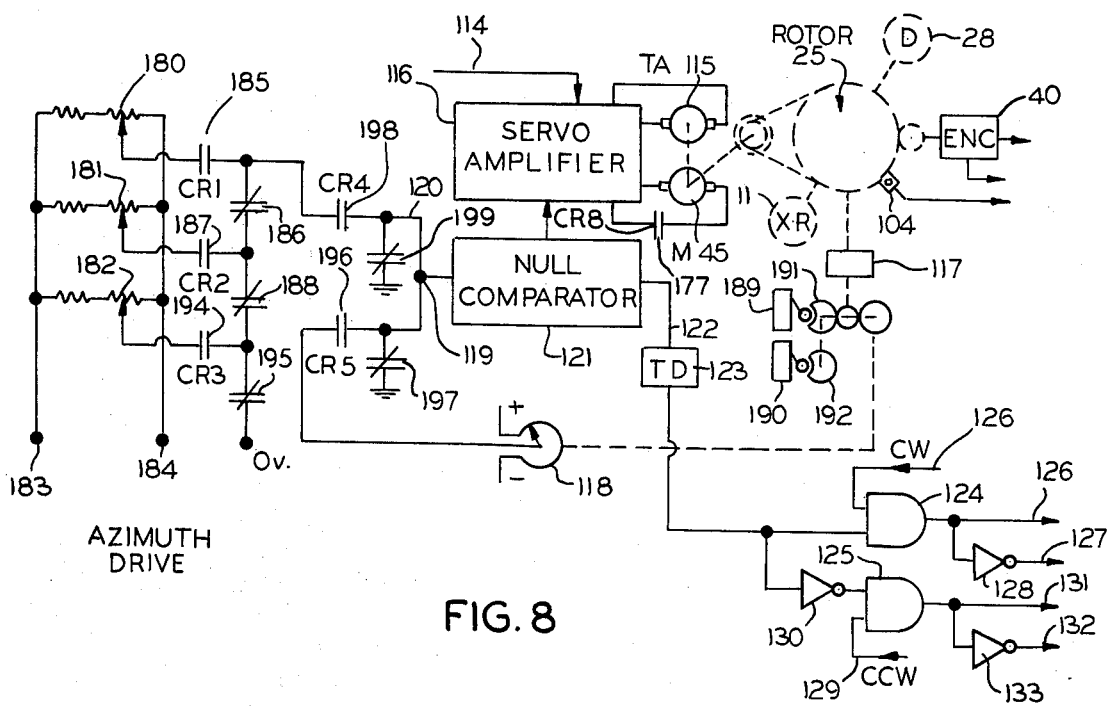
FIG. 8 is a block diagram of the azimuth drive.

In the preferred embodiment, the rotor 25 is driven synchronously with the frequency of the power line using an a-c synchronous motor for azimuth drive motor 45 as in FIG. 8. All parameters are then selected in accordance with prevailing power line frequency which is usually 60 Hz in this country and is sometimes 25, 40 or 50 Hz elsewhere. In other systems it may be desirable to drive the rotor 25 synchronously with multiples or submultiples of the power line frequency. This gives all the advantages of power line synchronization as mentioned herein with the added flexibility of providing more or less x-ray pulses as the needs of the system change. In the present example, numbers based on a 60 Hz line frequency will be used to demonstrate the preferred system.

Referring to FIG. 1, 4 and 8, the rotor 25 again has a ring gear 36 for rotating a shaft driven precision encoder 40. In this case, for reasons which will become evident, the gear ratio is such that one revolution of ring gear 36 results in 24 revolutions of the encoder shaft. The encoder produces a multiple of 60 Hz, namely, 360 pulses per shaft revolution so the pulse train A in FIG. 4 constitutes 8640 encoder pulses for each azimuth or full 360° rotor revolution. As in the previous embodiment, a second encoder output is a pulse B occurring only once per encoder shaft revolution. This pulse is coupled to AND gate 105 with a separate azimuth derived pulse C from sensor 103 which occurs once per azimuth revolution. Pulses B and C are phased to be coincident once per azimuth revolution and, when coincident, cause a pulse output from AND gate 105 which occurs as x-ray 0° and x-ray 360° at the latter angles were defined earlier. Since the two encoder outputs are part of the same shaft assembly, their relationship is invariant and the spatial relationships between x-ray 0° and 360° are invariants with respect to the rotor 25.

The encoder output train of 8640 pulses therefore becomes a line synchronous clock for spatially synchronizing the locations of the start, center and end points of each pulse and for establishing x-ray pulse duration. In the exemplary system, 288 x-ray pulses or exposures and views are taken during 360° of rotor rotation for each body layer. There are 1.25° between centers of the x-ray pulses. In another case 576 exposures are taken during 360° of rotor rotation, i.e. 15 encoder pulses and 0.625° between centers of x-ray pulses. More or fewer exposures could be made, depending on the image resolution that is required.

The period between x-ray pulses is determined by counting encoder pulses and this may be done in a microprocessor, not shown, which serves as a system controller or by the computer which would then perform the control functions. The duration is also determined by encoder pulse counts. In this example the period is 8640/288 or 30 encoder pulses between x-ray pulses. Since the rotor 25 is driven line synchronously, the x-ray pulses will occur synchronously with power line frequency. In the actual apparatus scan velocities of 12.5 and 6.25 rpm are provided for. At 12.5 rpm a scan takes 4.8 seconds so 4.8/288 equals 1/60 second which is the interpulse interval. At 6.25 rpm a scan takes 9.6 seconds so 9.6/288 equal 1/30 second which is the interval. These are synchronous periods for 60 Hz line frequency and those skilled in the art will be able to determine the adaptations required for other line frequencies.

In the case of the 4.8 second scan the duration of each encoder pulse is $1/6 \div 30$ or 0.555 milliseconds. For 9.6 second scans it is 1.11 ms. Hence, with a 4.8 second scan the counter can control the x-ray exposure pulses to any length in increments of 0.555 ms. Actually, the counter is programmed to control the exposures in increments of two encoder pulses for reasons which will appear.

In one version of the apparatus, the encoder pulse counter is part of a controller which is actually an Intel 8080 microprocessor and in another version the task is performed with the computer which also reconstructs the images from the data and performs other control functions.

Generally stated, all x-ray pulses are of $2n$ encoder pulse duration where $n$ is an integer. The center of the x-ray pulses are then $2n/2$ encoder pulses after exposure start.

The following tabulation established $n$ for the two speed example and different operator exposure entries.

| X-ray Exposure | "n" encoder pulses | |
|---|---|---|
| | 4.8 Sec Scan | 9.6 Sec Scan |
| 1.11 msec | 2 | — |
| 2.22 | 4 | 2 |
| 3.33 | 6 | — |
| 4.44 | — | 4 |
| 6.67 | — | 6 |

To further illustrate, the following tabulation indicates the relative count with respect to a count of zero at x-ray 0° = Azimuth 0° at the start, center and end of the first and last x-ray exposure pulse for the system in a 4.8 second scan mode with operator selected exposure times of 1.11, 2.22, or 3.33 msec. 0° is the azimuth angle measured from a point which, as explained earlier, is an arbitrary zero point and not x-ray 0°.

| | | Case of 4.8 Sec Scan | | | | |
|---|---|---|---|---|---|---|
| x-ray Exposure Time-msec. | x-ray Exposure # | Exposure Start Count | Exposure Center Count | Exposure End Count | CW Rotation Azimuth° at Exposure Center | CCW Rotation Azimuth° at Exposure Center |
| 1.11 | 1 | 29 | 30 | 31 | $\theta° + 1.25°$ | $\theta° + 358.75°$ |
| 1.11 | 288 | 8639 | 8640 | 8641 | $\theta° + 360°$ | $\theta°$ |

-continued

| | | | Case of 4.8 Sec Scan | | | |
|---|---|---|---|---|---|---|
| x-ray Exposure Time-msec. | x-ray Exposure # | Exposure Start Count | Exposure Center Count | Exposure End Count | CW Rotation Azimuth° at Exposure Center | CCW Rotation Azimuth° at Exposure Center |
| 2.22 | 1 | 28 | 30 | 32 | $\theta° + 1.25°$ | $\theta° + 358.75°$ |
| 2.22 | 288 | 8638 | 8640 | 8642 | $\theta° + 360°$ | $\theta°$ |
| 3.33 | 1 | 27 | 30 | 33 | $\theta° + 1.25°$ | $\theta° + 358.75°$ |
| 3.33 | 288 | 8637 | 8640 | 8643 | $\theta° + 360°$ | $\theta°$ |

From the above chart it will be evident that all exposures are symmetrical about a center count, which in this example is 30 counts in every layer and for any x-ray pulse duration.

For 50 Hz synchronous rotor drive systems scans could be made in 5.76 seconds for high speed and 11.52 seconds for low speed. The duration of each encoder pulse would be $(1/50) \div 30 = 0.6666$ ms for fast scan and 1.3333 ms for slow scan if the same encoder and gear ratio were used as in the above 60 Hz line frequency example assuming that 288 exposures per azimuth revolution were desired again.

Two of several important reasons for pulsing the radiation source should now be clear. One is that the interval between pulses provides time to clear or reset the multiple element detector and any signal integrators associated therewith of any residual effects of radiation flux or photon intensities representative of absorption by the body during a pulse at a preceding rotational angle. This assures unambiguous absorption data at every angular increment.

Another important reason for pulsing the x-ray source is that reduced radiation dosage to the examination subject is obtainable without loss of data quality since when the pulse exists radiation intensity can be as high as needed to get good data and between pulses the subject receives no x-radiation. In addition, system temporal response is improved due to more effective motion stoppage with the pulsed system.

Use in the tomographic apparatus of a fan-shaped x-ray beam and an x-ray detector that is responsive to photon intensity distribution or x-ray flux across the beam will now be considered in more detail. It may be noted that the prior art teaches dividing the x-ray beam into discrete rays or alternatively having a plurality of collimators disposed in front of detectors, respectively, to define discrete paths of cross-sectional dimensions similar to those of the body elements in a layer. Disadvantages of dividing the x-ray beam into a plurality of rays on the source side of the subject or collimating the emerged beam in front of the detectors are that in the first case some of the radiation from the source never reaches the body and is wasted and in the second case some of the radiation emerging from the subject falls between collimators and is not detected although the subject receives the radiation dosage.

These problems are overcome in the present invention by using an incident beam which is collimated into a fan-shape and which emerges in a fan-shape having a substantially continuous x-ray photon or flux distribution in combination with a detector means that has a continuous volume which functions to measure a spatial distribution of the x-ray flux of the emergent fan-shaped beam. The detector is constructed and arranged for receiving substantially all of the x-ray flux that emerges from the body and measures flux distributed within the angle of the fan-shaped beam.

Embodiments of suitable multicell detector means are described in copending application Ser. No. 676,282 filed Apr. 12, 1976, which is assigned to the same assignee as this application and is incorporated herein by reference. A preferred embodiment is shown in FIG. 4 of the cited application and in FIG. 23 of this application.

Figure 23:
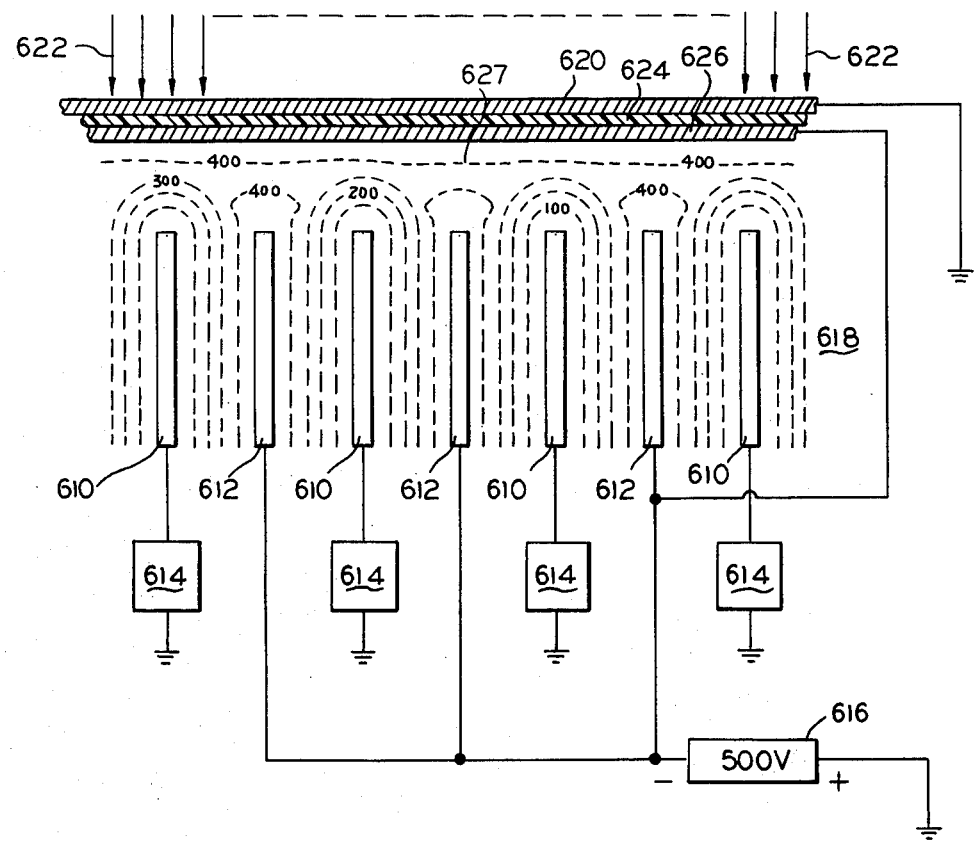
FIG. 23 is a diagram of an x-ray detector for use in the apparatus.

In FIG. 23 the detector chamber is omitted since its construction is shown in the copending application first cited herein. The detector is based on the phenomena of x-ray photons, which may be called flux collectively, interacting with atoms of a heavy gas to produce electron-ion pairs. Suitable gases are xenon, argon, krypton and molecular gases having an atomic weight greater than argon at approximately 10 atmospheres to approximately 50 atmospheres. If the electron-ion pairs are produced in a region between two electrodes of opposite polarity they will drift along the electric field lines and yield a net electric current. Thus, the current flow between electrodes is a function of the total number of x-ray photons interacting in the vicinity of the electrodes.

In FIG. 23 the electrodes comprise anode plates 610 and cathode plates 612 disposed in a manner described in the cited applications in a manner described in the cited applications in a high pressure gas ambient 18. The anodes 610 are grounded through current detecting means 614 and the cathodes 612 are maintained at a negative potential by a power supply 616 having a grounded positive terminal. A continuous distribution of incident x-ray photons or flux within the width of the fan-shaped beam is suggested by the arrows 622. X-rays 622 enter the detector through a thin conductive x-ray permeable window 620 in a direction substantially parallel to closely spaced anodes 610 and cathodes 612. Within limits, the closer the spacing of the electrodes the better will be the resolution of the detected photon intensities across the beam.

The window 620 forms a portion of the pressure vessel and is maintained at ground potential. A thin dielectric film 624 0.12 mm thick such as the film know by trademark Mylar or polycarbonate resin films is disposed on the inner face of window 620. A thin conductive electrode 626 which may, for example, be a 0.05 mm aluminum film is disposed on the surface of dielectric 624 opposite window 620.

Electrode 626 is connected to and maintained at cathode potential by power supply 616. The equipotential lines of the electric field thus produced in the space 627 between the window electrode 626 and collector electrodes 610 and 612 is illustrated by the dashed lines in FIG. 23 and they are labeled with their approximate potentials assuming a 500 volt power supply 616 is used. The electric field in this region is directed toward the anodes 610 so that electrons produced in that region tend to flow to the anodes where they are collected and measured by the current detector means 614.

Note that the active or photon sensitive volume is continuous over the length of the detector. Any sufficiently energetic photon entering volume 627 will result in current flow between electrodes in response to the ionizing event. When the electrodes 610 and 612 are as close as applied voltage permits, the detector has exceptionally fine resolution of the photon directions or distribution across the fan-shaped beam.

Figures 19, 20:
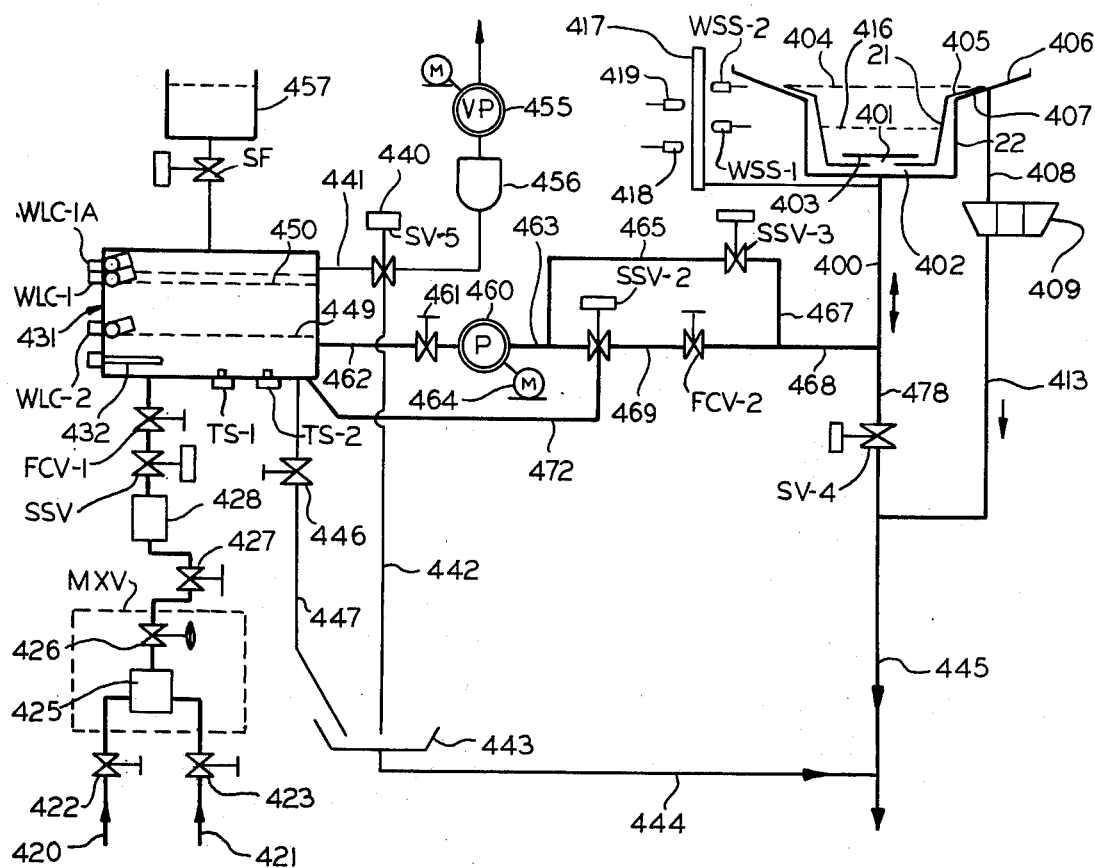
FIG. 19 is a schematic digram of an alternative water system for use in the scanning apparatus.
FIG. 20 is a schematic diagram of a system which permits obtaining x-ray data with a fan-shaped x-ray beam but does not require that the x-ray beam be pulsed.

In the embodiments thus far described, the fan-shaped x-ray beam was pulsed on and off at regular angular increments and the x-ray intensity signals from the multiple elements of detector array 28 were readout between pulses. FIG. 20 shows a system which allows retention of the benefits of using a fan-shaped x-ray beam but does not require that it be pulsed. The system permits rotating the x-ray beam at a constant angular velocity or in incremental angular steps without turning the beam off during the scan of a body layer. In general terms, the FIG. 20 system uses two banks of capacitors. While the capacitors in one bank are being charged in accordance with the x-ray intensities, the capacitors in the other bank are being readout and the two banks are switched alternately between their inputs from detector 28 and their outputs to data acquisition apparatus 75.

More specifically in reference to FIG. 20, detector 28 may be similar to the one described in co-pending applications Ser. No. 616,930, filed Sept. 26, 1976 or Ser. No. 676,282, filed Apr. 12, 1976. It comprises a large number of individual cells such as the one marked 510. The cells are bounded by common cathodes 511 and 512 and each cell has an anode such as 513. By way of example, in a practical case the detector 28 has 320 cells. More or fewer could be used. One of the readout leads 514 from a typical cell is shown connected in further circuitry but it will be understood that there are corresponding leads from the anodes in each of the cells.

Integrator capacitor banks 515 and 516 are used in this case. In bank 515, two illustrative capacitors 517 and 518 are shown but is will be understood that there are as many capacitors in the bank as there are cells to be readout from the detector 28. Each capacitor is in a switching circuit. A typical capacitor 517 is in circuit with a switch 519 which is shown as a singlepole double-throw mechanical switch such as a read switch but a transistor switch can be used as well. Switch 519 is illustrated as connected anode output line 514 from one of the cells to capacitor 517 so that the capacitor accepts charge from the detector cell as the fan-shaped x-ray beam is making its sweep. There are additional switches, not shown, similar to switch 519 connected to each of the cells 510 and each switch leads to a capacitor in bank 515. Switch 519 and its counterparts associated with bank 515 is controlled by a multivibrator 520 or its equivalent. There is a multivibrator for each switch such as 519. The switching rate of the multivibrator is controlled through a flip-flop 521 or an equivalent device which is timed by signals derived from and under the control of azimuth encoder 40. When all of the capacitors have integrated the charge from the detector cells for a moment, switch 519 is transferred under the influence of multivibrator 520 so that the charge on the capacitors such as 517 and 518 is readout by the data acquisition system symbolized by the block 75 in FIG. 20. Subsequent to readout of the data, and before the capacitors are reconnected, a short circuiting switch, symbolized by the block marked 521, having a control line 522 is activated and it discharges all of the capacitors in the bank to zero voltage. While the capacitors in bank 515 are accummulating charge through switches 519 which are in the positions shown at that time, the other set of switches marked 523 are connected to the data acquisition module 75 as shown so that the capacitors such as 524 and 525 can be read out simultaneously. Switches similar to 523 are controlled by individual multivibrators such as 526. Thus, the operating mode is to switch the groups of switches 519 and 523 for alternately reading out the detector elements in parallel or simultaneously and then transferring the integrated charge to the data acquisition module.

Figure 7:
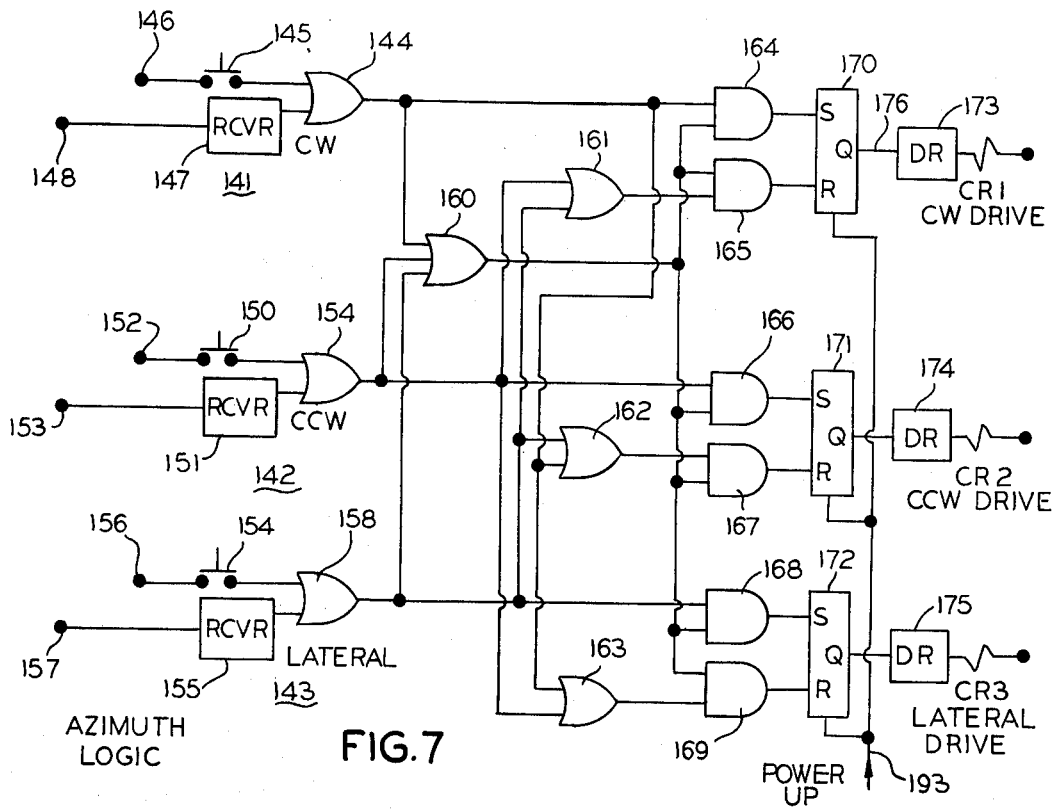
FIG. 7 is a diagram of one form of logic that is used for controlling scanner rotation or azimuth.

The azimuth drive and its control will now be discussed. Recall that the scanner or rotor 25 in FIG. 1 is driven rotationally by servomotor 45. The logic system and the azimuth drive system components are shown in FIGS. 7 and 8, respectively, to which reference is now made.

In FIG. 8, the azimuth drive servomotor 45 is shown schematically as being coupled in driving relationship to the scanner rotor 25. Motor 45 is also coupled to a tachometer 115 which delivers its signals in a feedback loop to a servo amplifier 116. The servo amplifier in turn controls the voltage applied to motor 45 and, hence, its rotational speed. Servo amplifier 116 normally receives a-c power over an input line 114. This power is obtained from a triac driver 291 shown in FIG. 6.

Figure 6:
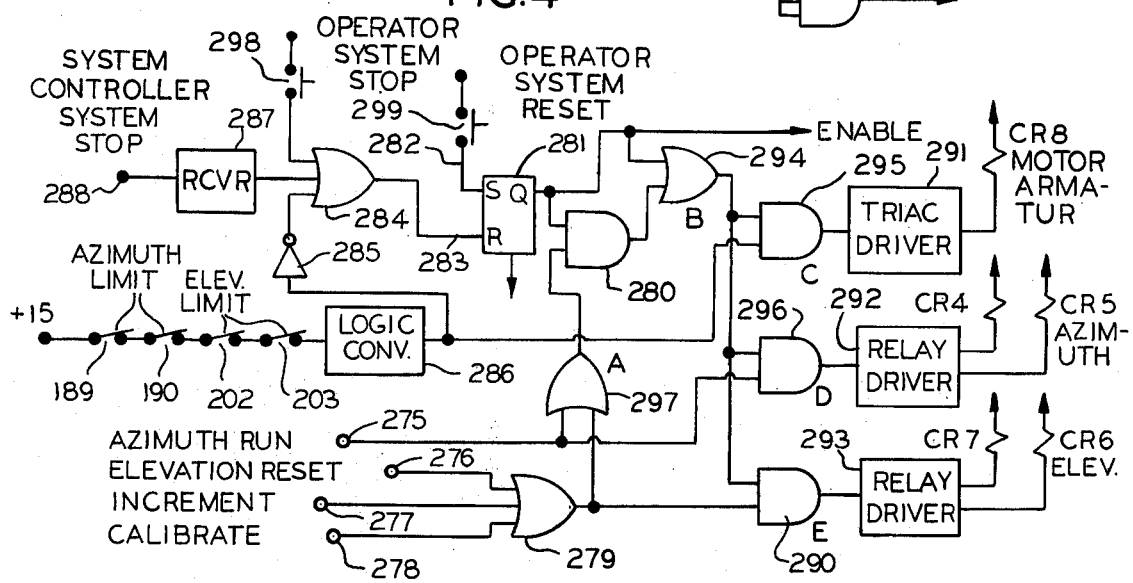
FIG. 6 is a block diagram illustrating some of the electrical components that are involved in stopping operation of the scanning apparatus.

The armature circuit of azimuth drive motor 45 has a normally open contact 177 which is caused to close for motor operation by relay CR8 in FIG. 6 if several requisite operating conditions are satisfied. Subsequently, in a discussion of FIG. 6, it will be shown that all elevator and rotor drive functions can be halted when certain conditions exist by deenergizing the triac driver and switching some relay contacts.

As described earlier, when the system is energized and the azimuth drive is operating, the timing pulse train is produced by encoder 40. By means of a gear train represented symbolically in FIG. 8 by the block 117, rotor 25 drives a potentiometer 118 which produces a voltage representative of the instantaneous rotor azimuth angle. Gear train 117 and potentiometer 118 are actually in box 41 in FIG. 1 but they are not visible therein. The arm of the potentiometer 118 from which the azimuth indicating voltage is obtained, is connected through a contact 196 of a relay coil CR5 which is shown in FIG. 6. Relay coil CR5 is energized any time a command is given for the rotor to drive through a particular angle if all conditions for drive are met. When contact 196 closes, contacts 197 and 199 of relay CR5 in FIG. 8 are opened. The signal from potentiometer 118 through contact 196 goes to a summing point 119 which is the input to a null comparator 121. Analog voltage signals of preset values corresponding with rotor rotational commands incidental to scanning the patient and setting up the patient are received over a conductor 120 which connects to summing point 119. How the analog voltage signals are generated and selected will be discussed later. The analog signals are fed through contact 198 in FIG. 8 which is controlled by a relay coil CR4 in FIG. 6. Null comparator 121 has its output connected to servo amplifier 116 and its input connected to summing point 119. When the command analog voltage on line 120 nulls the signal from potentiometer 118, the null comparator reacts by signaling the servo amplifier to deenergize rotor drive motor 45. As long as comparator 121 is not nulled, a signal appears on one of its output lines 122 in series with which there is a short time delay device 123. The signal on line 122 is for indicating to the controller part of the computer when the commanded direction of rotation and angular position of the rotor have been reached. The output signal from the comparator 121 constitutes one input of each of a pair of AND gates 124 and 125. When a clockwise signal is commanded, there is an enabling signal on input 126 of gate 124, thus, the output of gate 124 changes state when null is reached and this signal is delivered back to the controller through high and low driver lines 126 and 127 in the latter of which there is an inverter 128. When a counterclockwise command is given, input 129 of AND gate 125 is enabled and the differential signal or a zero signal, indicating null, is delivered to the other input of gate 125 through an inverter 130. When null is reached, the output of gate 125 changes state and this signal is indicated to the controller over lines 131 and 132, in the latter of which there is an inverter 133.

The azimuth drive or rotor drive motor 45 can be signaled to drive with a manually generated command. Such commands are used to establish the rotor 25 in certain positions when setting up the patient and also when the apparatus is being serviced.

A logic system for typifying significant logic functions related to the azimuth drive is shown in FIG. 7. This system has three command signal input stages 141, 142 and 143. Stage 141 is involved in controlling clockwise scanner rotation. Stage 142 is involved in counterclockwise scanner rotation. Stage 143 is for locating the scanner laterally of the longitudinal axis of the subject when the subject is being prepared for an examination. This permits viewing the breast through the transparent water containers to assure that the breast is properly aligned and positioned for scanning. One view is taken when the scanner is longitudinal and the other when it is lateral. The scanner is turned longitudinally relative to the patient to avoid interference with the operator's line of sight. For loading the patient, the scanner is in the lateral position to provide clearance for tilting the patient support.

In FIG. 7, clockwise (CW) rotor controlling input stage 141 has an OR gate 144 with two inputs. One input receives a signal through a manually operable push button switch 145 which is used when the operator desires to set a particular azimuth angle or cause clockwise rotation of the scanner. The signal may be obtained from a logic level voltage source, not shown, connected to input terminal 146. The other input of OR gate 144 has a receiver 147 in series with it and the receiver is provided with command signals on input terminal 148. These signals are provided without operator involvement during automatic scanning. The receiver 147 is a commercially available light coupled isolator.

Input stage 142, for controlling counterclockwise (CCW) rotations, of rotor 25, also has a push button 150, a receiver 151, input signal terminals 152 and 153 and an OR gate 154. Lateral control stage 143 similarly has a push button 154, a receiver 155, input terminals 156 and 157 and an OR gate 158. Automatic command signals such as are received on input stage terminals 148, 153 and 157 are short duration pulses. Any input to a stage will cause one of the OR gates 144, 154 or 158 associated therewith to go high. The logic is such that commands cannot conflict. When any of the outputs of the OR gates 144, 154 or 158 in the input stages are caused to go high, one of the relay coils CR1, CR2 or CR3 will be energized exclusively. This causes an appropriate analog voltage to be applied by way of line 120 to summing point 119 at the null comparator 121 in FIG. 8 and results in rotor 25 turning to the proper azimuth angle and in the proper direction and then stopping when there is no difference between the analog voltage and the voltage from potentiometer 118.

Considering FIG. 7 further, the logic circuitry comprises OR gates 160-163, AND gates 164-169 and flip-flops 170-172. The output signals from the respective flip-flops are transmitted through drivers 173-175 associated with the relay coils CR1-CR3 that select the analog voltages through contacts 185, 187 or 194, respectively, in FIG. 8.

Functions of the azimuth logic circuit of FIG. 7 will now be explained further. Assume that an automatic clockwise pulse command signal is received on input terminal 148 or a manual signal is supplied by operation of push button 145. The output of OR gate 144 will go high. This will switch the output of OR gate 160 high. The two high output signals from OR gates 144 and 160 are applied to the inputs of AND gate 164 and its output will go high, thus setting the output 176 of flip-flop 170 high. This will energize relay CR1 and close contact 185 in FIG. 8. Servomotor 45 in FIG. 8 will then drive rotor 25 to the desired azimuth angle for a clockwise scan. How this is achieved will be discussed further shortly hereinafter. When the inputs to AND gate 164 are both high, it will be noted that one of the inputs to adjacent AND gate 165 will be high and the other input, leading from OR gate 161 will be low so that there is no conflicting tendency to reset flip-flop 170 at the same time that its output 176 is set high since the output of AND gate 165 will remain low. The other flip-flops 171 and 172 will, however, be forced to their reset state, that is, with low or no output signals. Flip-flop 171 will be in the reset state because, at this time, both inputs to AND gate 167 are high and its output is high, thus providing a reset signal to flip-flop 171. On the other hand, one input to AND gate 166 will be low since the output of OR gate 154 is low and the other input to this AND gate will be high due to the output of OR gate 160 being high.

At the same time, flip-flop 172 will be held in its reset state, that is, with no output since its associated AND gate 169 will have two high inputs and the high output, thus causing reset. The tendency to set flip-flop 172 will not be present because the output of its associated AND gate 168 will be low due to one of its inputs being high and the other input from OR gate 158 in the lateral command stage being low.

When a counterclockwise command pulse is received on input terminals 153 or by operation of push button switch 150, the output of OR gate 154 will go high, thus causing the output of OR gate 160 to go high. This makes the lower input terminals of AND gate 164 high but its upper input is still low so the gate 164 has no output and flip-flop 170 is not set. However, both inputs to AND gate 165 go high and its output goes high so that flip-flop 170 is forced to reset. Flip-flop 172 will also be forced to reset by reason of the output of AND gate 169 being high due to both of its inputs being high. One of the high inputs of AND gate 169 results from the high output of OR gate 160. The other high input results fron the high output of OR gate 160. The other high input results from the high output of OR gate 163 which was switched by the output of OR gate 164 going high. There will be no tendency to set flip-flop 172 because the output of associated AND gate 168 is low due to the output of OR gate 158 being low in the absence of a lateral command signal. The lower input of AND gate 167 associated with flip-flop 171 will be high but its upper input will be low so there will be no output from AND gate 167 which would tend to reset the flip-flop. Both inputs to AND gate 166 will, however, be high and its output will be high so as to set flip-flop 171 and energized relay CR2. This causes application of an analog voltage to summing point 119 in FIG. 8 and causes the azimuth motor 45 to drive the rotor 25 to a predetermined angular position.

For the sake of brevity, occurrences upon receipt of a lateral command signal in stage 143 will not be traced in detail. One skilled in the art can easily see, however, that upon receipt of such signal, both inputs to AND gate 168 associated with flip-flop 172 will go high as will its output so that flip-flop 172 will set and energize relay CR3 and an analog voltage corresponding with the rotor 25 being positioned laterally will be applied to summing point 119 in FIG. 8. The other flip-flops 170 and 171 will be forced to reset by virtue of both inputs of their associated AND gates 165 and 167 being high so as to force reset of their flip-flops.

Selective energization of relay coils CR1, CR2 and CR3 in FIG. 7 results in applying a predetermined analog voltage signal to summing point 119 at the input of the null comparator 121 in FIG. 8 as has been mentioned. These voltages are obtained from potentiometers 180, 181 and 182 in FIG. 8. The common terminals of the potentiometers are connected to a voltage source, not shown, by way of terminals 183 and 184. Assume that relay coil CR1 in FIG. 7 is energized to dictate clockwise rotation of the scanner or rotor 25. This will result in the normally open contact 185 of relay CR1 in FIG. 8 closing and the normally closed contact 186 opening. By other means which will be described, normally open contact 198 of a relay CR4, to be discussed in reference to FIG. 6, will be closed and its adjacent normally closed contact will open to supply the preset analog voltage from the wiper of potentiometer 180 to summing point 119. If the potentiometer 118 that is driven by the rotor 25 is not producing a balancing voltage, the voltage differential will cause the null comparator to drive the servo amplifier 116 and azimuth motor 45. Rotation of rotor 25 will result in driving potentiometer 118 until its output voltage balances that of the analog input signal from potentiometer 180, and when null is reached, the servo amplifier 116 will be deenergized and azimuth drive motor 45 will stop.

Similarly, when counterclockwise rotation controlling relay coil CR2 in FIG. 7 is energized, its associated contacts 187 and 188 in FIG. 8 will close and open, respectively, and a voltage will be applied to summing pont 119 for comparison with the voltage from rotor driven potentiometer 118 that is representative of the present azimuth of rotor 25.

Of course, operation of relay coil CR3 in response to a lateral command signal will result in the analog voltage from potentiometer 182 being applied to summing point 119 for comparison with the existing potential from potentiometer 118. When coil CR3 is energized, its contact 194 closes and contact 195 opens so the analog voltage is applied. In both of the latter cases as in the former, azimuth drive motor 45 will be energized and rotor 25 will be driven until null is reached and it will stop or coast until it is otherwise stopped. In all cases, the potential from azimuth angle indicating potentiometer 118 is applied through contacts 196 which is controlled by the system stop circuit shown in FIG. 6 which will be described later.

Before leaving FIG. 8, it should be noted that there are limit switches 189 and 190 operated by cams 191 and 192. Switch 189 opens in response to the rotor 25 having reached its ultimate position which may be as much as 90° more than the x-ray-off point of the clockwise direction. Limit switch 190 opens when counterclockwise rotation has gone beyond the x-ray-off point by about 90°.

Further in reference to FIG. 7, OR gates 161, 162 and 163 initialize the output flip-flops 170-172 and guarantee that unselected commands will reset the unselected flip-flops 170-172 to zero. Also provided in this FIG. is a line 193 on which a control signal resets all of the Q outputs of flip-flops 170-172 to zero under circumstances which will be described.

Having described the azimuth logic and the azimuth drive system in connection with FIGS. 7 and 8, attention is now invited to means for translating the rotor from body layer to body layer, said means being more specifically the elevator logic and elevator drive. These will be explained in reference to FIGS. 9-11 primarily. The elevator is designated by the numeral 39 in FIG. 1 and has the rotor 25 which is driven in azimuth mounted on it. The logic and drive system to be described now is applicable to any translator, whether it steps vertically or horizontally, in x-ray scanning apparatus and whether it is specialized for breast examination or is adapted for scanning other parts of the body or the whole body.

The scanner translational system, which in the case of the breast scanner moves up and down along a vertical line, is called an elevator 39 and shown in FIG. 1. One function of the elevator 39 is to permit orbital scanner or rotor 25 to be incremented to the next tissue layer after each orbital scan is completed. Another function is to allow the orbital scanner to be raised to an initial level in preparation for making a scan sequence to assure that the scans will start at the proper level. The elevator control system is setable for terminating the scanning sequence when the lowermost level or apex of the breast or the desired limit of some other body part is reached. The elevator is incremented downwardly automatically during a layer scanning sequence in this example.

The elevator 39 is also responsive to a command to go to calibrate level. This is a position or level at which the x-ray may be turned on by the operator and projected through a repeatable level of the breast container and the water therein for the purpose of zeroing the detectors immediately before examining each subject or at such other times as are desired.

The elevator 39 is also provided with a drive stop, to be explained in detail later in connection with FIG. 6. The stop system responds to system controller commands that take precedence over any previously issued command. An elevator system reset entry command causes the elevator to be driven to home position which, in this example, is its uppermost position although home could optionally be the lowermost position.

Figure 11:
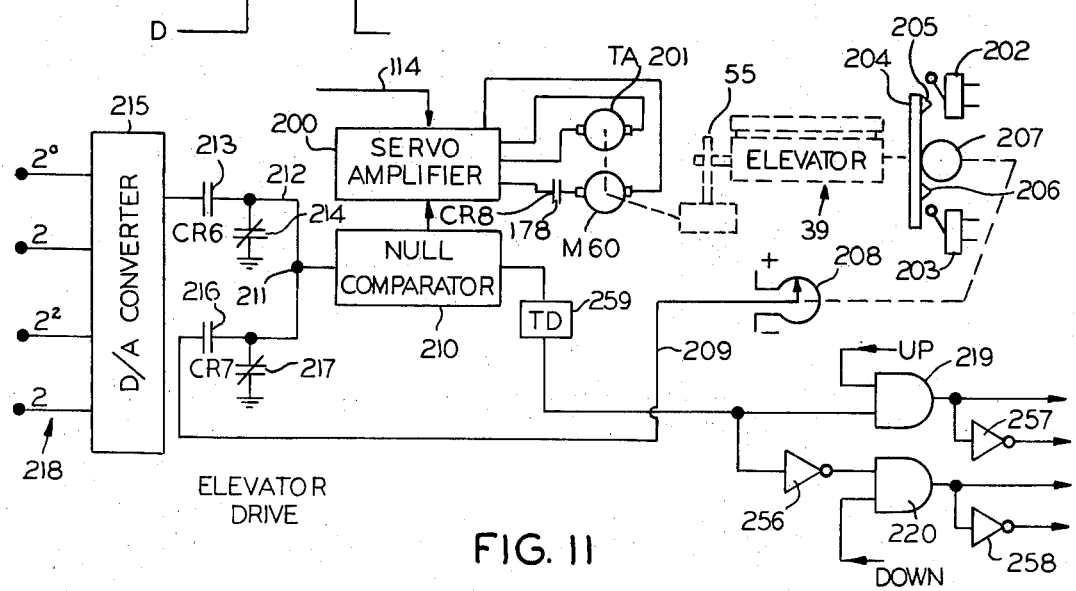
FIG. 11 is a diagram of the elevator drive in the scanning apparatus.

The elevator drive system is depicted in FIG. 11. The elevator is shown symbolically and marked with the number 39 as it is in FIG. 1. It is driven vertically by lead screws such as 55 which are driven by servomotor 60. The armature circuit of elevator drive motor 60 has a normally open contact 178 which is caused to close for motor operation by relay CR8 in FIG. 6 if several requisite conditions for motor operation are met. The servomotor is powered from a servo signal amplifier 200. The amplifier is supplied with a-c power by way of line 114 from the triac driver in FIG. 6 similarly to the servo amplifier 116 in the previously discussed azimuth drive illustrated in FIG. 8. A tachometer TA-201 is driven by the servomotor 60 shaft. The tachometer produces a feedback signal to the amplifier 200 which results in the motor 60 operating at a constant speed. A limit switch 202 is provided for assuring discontinuance of elevator drive for the uppermost acceptable level limit of the elevator. A lower level limit switch 203 is also provided. The limit switch operator is symbolized by a toothed rack 204 on which there are upper and lower limit switches 202 and 203, respectively. The rack also drives a pinion 207 which is coupled to a elevator level indicating potentiometer 208. The output voltage on line 209 from potentiometer 208 at any time is functionally related to elevator level.

A null comparator 210 whose output state determines operation of servomotor 60 has its input connected to a summing point 211. As will be explained, analog voltage signals corresponding, respectively, with the various levels to which the elevator is to be driven, are supplied to summing point 211 over a line 212. The balance voltage signal from potentiometer 208 is also supplied to the summing point over line 209 through contact 216 in FIG. 11 which is controlled by relay CR7 of FIG. 6. Whenever there is a difference between the analog voltage representative of an elevator level command and the voltage on potentiometer line 209, the difference is sensed by the null comparator which causes motor 60 to drive the elevator and potentiometer 208 until the difference is reduced to zero or nulled and the motor stops. Connected in line 212 leading to summing point 211 are a pair of contacts 213 and 214 that are controlled by relay CR6 whose location and function will be described later in connection with the FIG. 6 system stop circuit. Contact 213 is supplied from a digital-to-analog converter 215 with level representing analog signals. Another pair of contacts in the potentiometer line are marked 216 and 217. These are controlled by a relay coil CR7 in FIG. 6 which will be described later. For the present time it is sufficient to observe that when relay contacts 213 and 216 are closed and 214 and 217 are open, it is possible to supply the signals which correspond with desired elevator levels and the balance signal from the converter 215 and potentiometer line 209, respectively, to summing point 211. This causes elevator drive until null is reached. When the elevator step resulting from an analog signal from D/A converter 215 is being attained, a signal is delivered from comparator 210 to the computer control by way of the outputs of one or the other of a pair of AND gates 219 and 220. The gates are inputed from the comparator through a short time delay 259. Gate 219 gets an up enable signal when up is commanded. Gate 220 gets a down enable signal when the elevator is commanded down. When the elevator is commanded to go up, both inputs to AND gate driver 219 are high until null is reached. At this time inverter 256 assures that the other down AND gate will be disabled. When the output from comparator 210 is opposite in polarity, down AND gate 220 has both inputs enables. Inverters 257 and 258 allow for a low output signal along with a high one.

Digital to analog converter 215 need not be a very sophisticated type. In a sense it serves the purpose of a voltage divider with several taps that can be connected selectively to contact 213 such that the step voltages correspond with different levels of the elevator. The proper tap can be considered as being selected by whatever four digit binary digital number appears on the four input terminals 218 of the converter. With four input terminals, of course, the highest possible binary number that can be supplied to the converter is 15. Including zero, this permits the elevator to be stepped to anyone of 16 discrete levels or body layers. Of course, different numbers of steps may be used in a breast scanner to enchance resolution of each plane scanned. The body scanner version provides for transporting the patient for a sufficient number of planes or steps to cover that part of the length of the body which is selected for examination.

Figure 9:
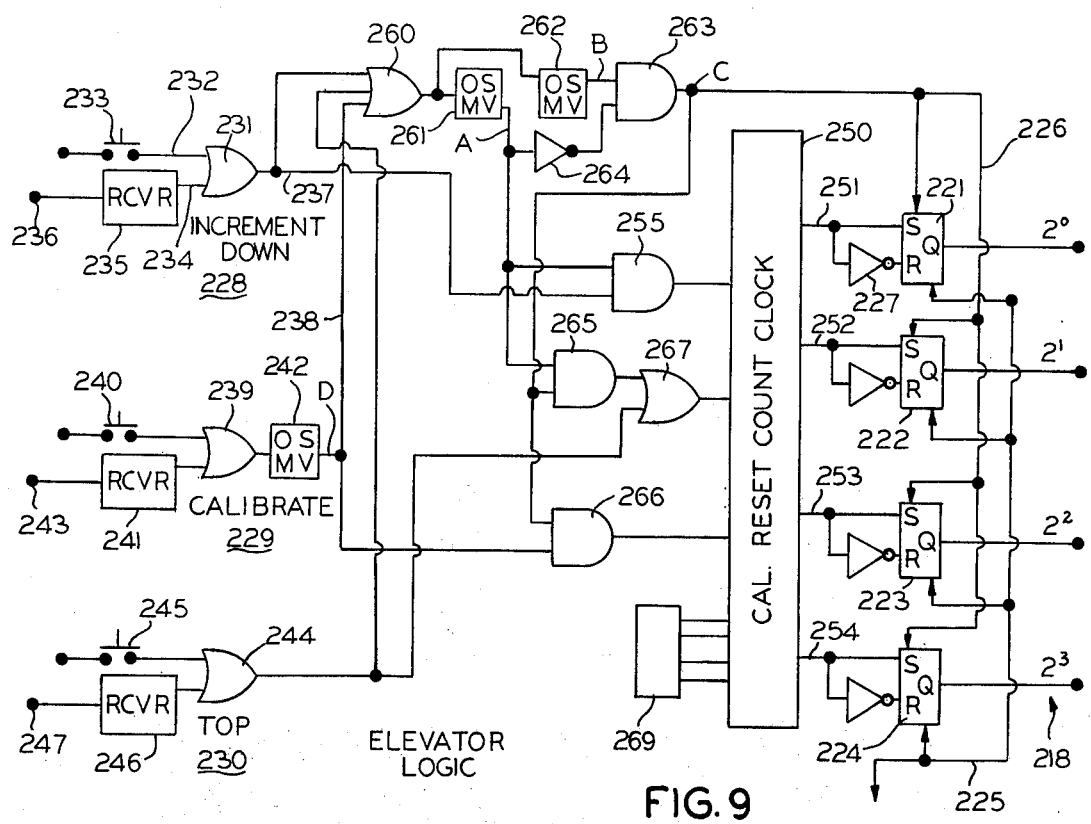
FIG. 9 is a diagram of illustrative logic circuitry for controlling the translating mechanism or elevator in the scanning apparatus.

An elevator logic circuit for demonstrating the main concepts involved in controlling the elevator is depicted in FIG. 9. The four output terminals 218 in FIG. 9 connect to those marked with the same number in FIG. 11. The binary number obtainable are 0 to 15 as explained above. The least-to-most significant digits are marked with exponential numbers in FIG. 9. Whether a particular digit is 1 or 0 depneds upon the output state of each in a group of flip-flops 221-224. A power-up reset bus 225 connects to all of the flip-flops so that a suitable signal thereon will set all of the flip-flops 221-224 outputs to zero. Another bus 226 also connects to all of the flip-flops. When bus 226 has a high signal on it, all of the flip-flops are enabled. That is, they are susceptible to having their output states switched from low to high by a high signal on their set inputs marked S. As typified by flip-flop 221, there is an inverter 227 connected between each set line and the reset terminal, R of each flip-flop. This assures that when any set line goes high, such as to change a state of the flip-flop output, a zero in placed on the reset terminal so that the input to a flip-flop set terminal is made zero, the output of the inverter will go high to effect reset and made the output of the flip-flop low.

Refer now to the left region of FIG. 9. It has three command signal input stages 228-230. Consider the uppermost state 228. It is for handling command signals, either manual or automatic, that dictate incrementing the elevator 39 downwardly. Stage 228 has an OR gate 231. One of its inputs 232 has a manually operated push button switch 233 in it. Push button switch 233 is connected to a logic voltage source, not shown, such that if the push button switch is closed, the output of OR gate 321 will go high and cause the elevator to increment one step down for reasons that will be explained. Another input 234 of OR gate 231 has a receiver 235 in series with it. The receiver is simply an isolator of the optical type. Automatic command signals for incrementing the elevator one step down at the end of each scan during an examination are received from the system controller on input terminal 236. These pulse command signals also cause the output of OR gate 231 to go high and effect one of the elevator's downward steps.

Stage 229 is for driving the elevator to a level where the fan-shaped x-ray beam and detector are passing through a plane of the breast containers at which calibration may be made with the x-ray power on before a scanning sequence is initiated as was mentioned earlier. Stage 229 comprises an OR gate 239, a manual push button 240, a receiver 241 and a one-shot multivibrator 242. Movement of the elevator to the calibrate level can be caused by depressing push botton switch 240 momentarily. Automatic pulse command signals for moving the elevator to calibrate position are delivered from the system controller to the input terminal 243. A momentary command signal through push button switch 240 or a pulse command signal through input terminal 243 causes the output of OR gate 239 to change state and effect the calibration mode.

Input stage 230 is for signaling the elevator to go to its uppermost or home position. It is subject to manually caused command signals and pulse signal commands from the system controller. Stage 230 comprises an OR gate 244, a push button switch 245, an optical isolating receiver 246 and an input terminal 247 for receiving pulse command signals from the controller. Push button 245 is supplied from a separate voltage source as was indicated above in respect to the other push button switches.

Elevator commands are executed through a circuit module which, in a commercial embodiment, is a model K220, Digital Equipment Corporation unit shown in block form and marked 250 in FIG. 9. Four of the available outputs 251-254 are depicted on module 250. When any of the outputs goes high, its associated flip-flop in the group 221-224 is set and the Q output of the flip-flop constitutes a binary 1. The opposite happens when a module 250 output goes low. Its associated flip-flop is then reset and the Q output of the flip-flop in the group of outputs 218 goes to zero so that the sequence of 16 binary numbers may be formed with the four flip-flops.

Module 250 has a clock and a counter. On connection to the module is from an AND gate 255. When an increment down signal is delivered through stage 228, the output of AND gate 255 goes high. When the output of AND gate 255 goes high, module 250 counts a clock pulse and causes the binary number 0001 to appear on the outputs $2^0$ to $2^3$ of flip-flops 221-224. The next command pulse results in another output pulse from AND gate 255 and the binary output changes to 0010. Consecutive command pulses ultimately cause the binary number 1111 or decimal 15 to be produced unless the flip-flops are reset automatically earlier because of the length of the breast having been scanned.

Figure 10:
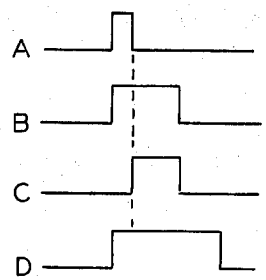
FIG. 10 shows some waveforms that are useful for explaining the elevator logic functions.

The complete operating mode of the elevator logic in FIG. 9 will now be described in conjunction with FIG. 10. The logic elements are OR gate 260, one-shot multivibrators 261 and 262, and AND gate 263, and inverter 264, AND gates 265 and 266 and an OR gate 267. The circuitry will be described concurrently with its operating mode. Assume first that a pulse signal is received through stage 228 to cause the elevator to increment down one step. The output 237 of OR gate 231 will go high. This makes one input of AND gate 255 high. It also switches OR gate 260 so its output will go high. Whenever the OR gate 260 output goes high, one-shot multivibrator 261 is triggered to produce the pulse A in FIG. 10 which appears on the line marked A in FIG. 9. With line A high momentarily, the two inputs to AND gate 255 are high and its output is high, thus causing the module 250 to execute an output binary number change. Multivibrator 262 receives an input signal from the output of OR gate 260 concurrently with multivibrator 261. The output signal from multivibrator 262 is marked B in FIG. 9 and in the waveform illustration of FIG. 10. Pulse signal A is inverted with inverter 264 and applied to one input terminal of AND gate 263. When A goes low, as can be seen in FIG. 10, B is still high and the other input ot AND gate 263 goes high, due to inversion of A. This causes the output of AND gate 263 to high and deliver an enable signal to the various flip-flops 221-224. The count of the module 250 is then registered. Note that when C is high, one input to each of the AND gates 265 and 266 is also high but their outputs do not change because their other inputs are low. Thus, no conflict can occur between step count, reset and calibration signals. AND gate 265 is disable because A has gone low before C has gone high. AND gate 266 is disabled because, although C is high, the other input remains low.

To drive the elevator 39 to calibrate level, a command pulse is delivered to OR gate 239 in stage 229. The output of OR gate 239 goes high and the pulse D appears on its output. Pulse D rises, and input to OR gate 260 goes high so its output goes high to trigger the two one-shot multivibrators 261 and 262. C goes high to produce an enable signal which is applied to flip-flops 221-224. When C goes high after D, they are both high as are both inputs to AND gate 266. Hence, its output goes high which triggers the module to set the binary number of flip-flops 221-224 corresponding with whatever level has been selected for calibrating. A programming jumper assembly symbolized by the block 269 is provided. In calibration mode, the elevation level is set by the jumpers. Other programming devices could be substituted.

The elevator is driven to its top, uppermost or home position by a command signal through stage 230. Such a signal causes the output of OR gate 244 to go high. This signal is delivered as an input to OR gate 260 which triggers the one-shot multivibrators 261 and 262 and ultimately results in the C waveform being produced which enables the flip-flops 221-224 for making a change. The high output from OR gate 244 is also applied to an input of OR gate 267 whose output changes state. This dictates that module 250 will produce a binary number 0, corresponding with the top or reset position of the elevator.

Because all of the binary numbers are sorted in the flip-flop group 221-224, as they are produced, the numbers are continuously applied to the digital-to-analog converter 250 in FIG. 11 by way of terminals 218. This drives the elevator servomotor 60 until potentiometer 208 produces the null signal corresponding with the applied signal and the motor stops.

An important aspect of the control system is the stop system whose circuit diagram is shown in FIG. 6. This circuit has several important functions. It assures that there is operator involvement in connection with activating either the azimuth or elevation drives. It provides a means for preventing azimuth and elevation motor drives when either drive is in a limit position, such means being independent of the servo drive control. It provides a means for a system stop command to stop the azimuth and elevation motor drives both through normal servo drive control and redundantly through armature circuit control. It allows for activation of system stop either by operator push button command or automatically by the system controller when an abort scan is indicated for any of several reasons, such as scan speed being improper. It provides a means that requires operator involvement before either the azimuth drive or elevator drive can be reactivated following either a system stop command or a limit switch activation.

In FIG. 6, relay coils CR4-8 are shown. Relay CR8 must be energized for redundant safety contacts 177 in the armature circuit of motor 45 in FIG. 8 and 178 in the armature circuit of motor 60 in FIG. 11 to close and permit operation of these motors. Relays CR4 and CR5 control contacts 198, 199 and 196, 197 in the azimuth drive circuit of FIg. 8. Relays CR4 and CR5 must be energized for the azimuth drive motor to be activated. Relay CR6 and CR7 control contacts contacts in the elevator drive system in FIG. 11. CR6 controls contacts in the elevator drive system in FIG. 11. CR6 controls contacts 213 and 214 and CR7 conrols contacts 216 and 217. Deenergization of any of these relays will cause all drives to stop. They must all also be energized to start any drive.

The functions and construction of the system stop circuit in FIG. 6 will be described concurrently. Assume that flip-flop 281 has been initialized by a power up reset signal. At this time enabling line 289 will be low or at the logic zero. This results in both inputs to AND gate 280 and both inputs of OR gate 294 being low. The output of OR gate 294 will then be low and AND gates 295-296 and 290 will be disabled, thus preventing an enabling of the CR driver circuits.

The operator may take action to enable the system by closing momentary push button switch 299 to thereby apply a high going set signal over line 288 to flip-flop 281 and this causes its Q output and enabling line 289 to go high. By way of OR gate 294, the common input to AND gates 295, 296 and 290 go high. However, if any of the azimuth switches 189 or 190 or the elevator limit switches 202 or 203 are open, then the logic voltage level converter 286 maintains a low on the other input to AND gate 295, preventing enabling of CR8, while simultaneously through inverter 285 and OR gate 284 causing flip-flop 281 to reset and line 289 to go low, thereby removing the enable signals from the common AND gates 295, 296 and 290. However, if the limit switches were all closed then flip-flop 281 would have reset, and both inputs to AND gate 295 would be high, enabling triac driver 291 to energize CR8, closing contacts 177 and 178 in the armature circuits of both the azimuth and elevation motors, thereby enabling these motors to respond to servo commands.

Note that if any limit switch were initially open and then subsequently closed, a system reset entry with push button switch 299 would be required to enable line 289 and the drivers for relays CR4-8. An open limit switch would make the output of logic converter 286 low and this signal would be changed to a high one with inverter 285 so that the output of OR gate 284 would go high and a reset pulse would be applied to flip-flop 281 to disable line 289. Thus, setting the system with push button switch 299 would be required even though the limit switch reclosed.

The driver systems are also stopped by automatic commands from the system controller. A high going command signal on line 288 is coupled through opto-isolator receiver 287 so as to make the output of OR gate 284 go high and rest flip-flop 281. The azimuth and elevator drives can also be stopped at any time by the operator by pressing push button switch 298 which provides a logic high signal that is coupled through OR gate 284 to reset flip-flop 281. Thus, if there is an operator system stop signal provided with switch 298 or an automatic system stop signal applied on line 288, the output line 289 of flip-flop 281 will be disabled and the relays CR4-CR8 will be deenergized. Again, the operator must become involved by providing a reset entry signal with push button 298 before the relays can be energized again.

Command signals for the azimuth motor to run are applied on line 275. An azimuth run signal is coupled through OR gate 297 so as to raise one input to AND gate 280, but AND gate 280 will not enable CR8 unless line 289 is enabled. In line 289 is enabled, however, the azimuth relay driver 292 will be switched and relays CR4 and CR5 will be energized, causing contacts 196, 197 and 198, 199 in the FIG. 8 azimuth drive circuit to switch, allowing the servo to accept azimuth drive commands through contacts 185, 187 and 194 which are controlled by relays CR1, CR2 and CR3, respectively, in FIG. 7. As indicated above, the azimuth drive may be stopped at any time at the will of the operator or with a system command delivered to OR gate 284 by way of push button 298 or a stop signal from the system controller applied to line 288.

High going command signls for resetting the elevator in home position, or for incrementing it in steps up or down, or for locating it at calibrate level are applied selectively to inputs of an OR gate 279. Any high input signal will cause the output of OR gate 279 to go high and this high signal will be transmitted through OR gate 297 to an input of AND gate 280 and directly to AND gate 290 to enable CR6 and CR7 to relay driver 293. CR6 and CR7, when energized, close contacts 213 and 216 in FIG. 11 to thereby permit summation of the position signal through contact 216 and an analog signal for the desired position through contact 213 so that the elevator servo drive will run until null is reached as was explained earlier.

The cable take-up mechanism which is designated generally by the number 70 in FIG. 1 will now be described primarily in reference to FIGS. 12-15.

As previously explained, rotor or scanner arm 25 rotates more than a full revolution in each direction. A large number of cables and other conductors which lead from outside of the apparatus to the x-ray source 11 and to the detector assembly 13 must be swung through these large opposite azimuth angles. The group of cables and other conductors are designated generally by the reference numeral 301 at the bottom of FIG. 12. Exemplary cables in the group are the high voltage cables leading to the x-ray source 11. Other cables handle the x-ray tube filament current. There are conductors for supplying the stator which drives the rotating anode of the x-ray source and cables for the detector data acquisition devices and for power supply, for example. The new take-up device shown in detail in FIGS. 12-15 prevents the cables from becoming entangled in the mechanism of the apparatus. It also prevents the cables and other conductors from being sharply bent, overstressed, and entangled with themselves. Moreover, it handles the cables in such manner that they cause only unsubstantial resistance to rotor rotation.

Figure 12:
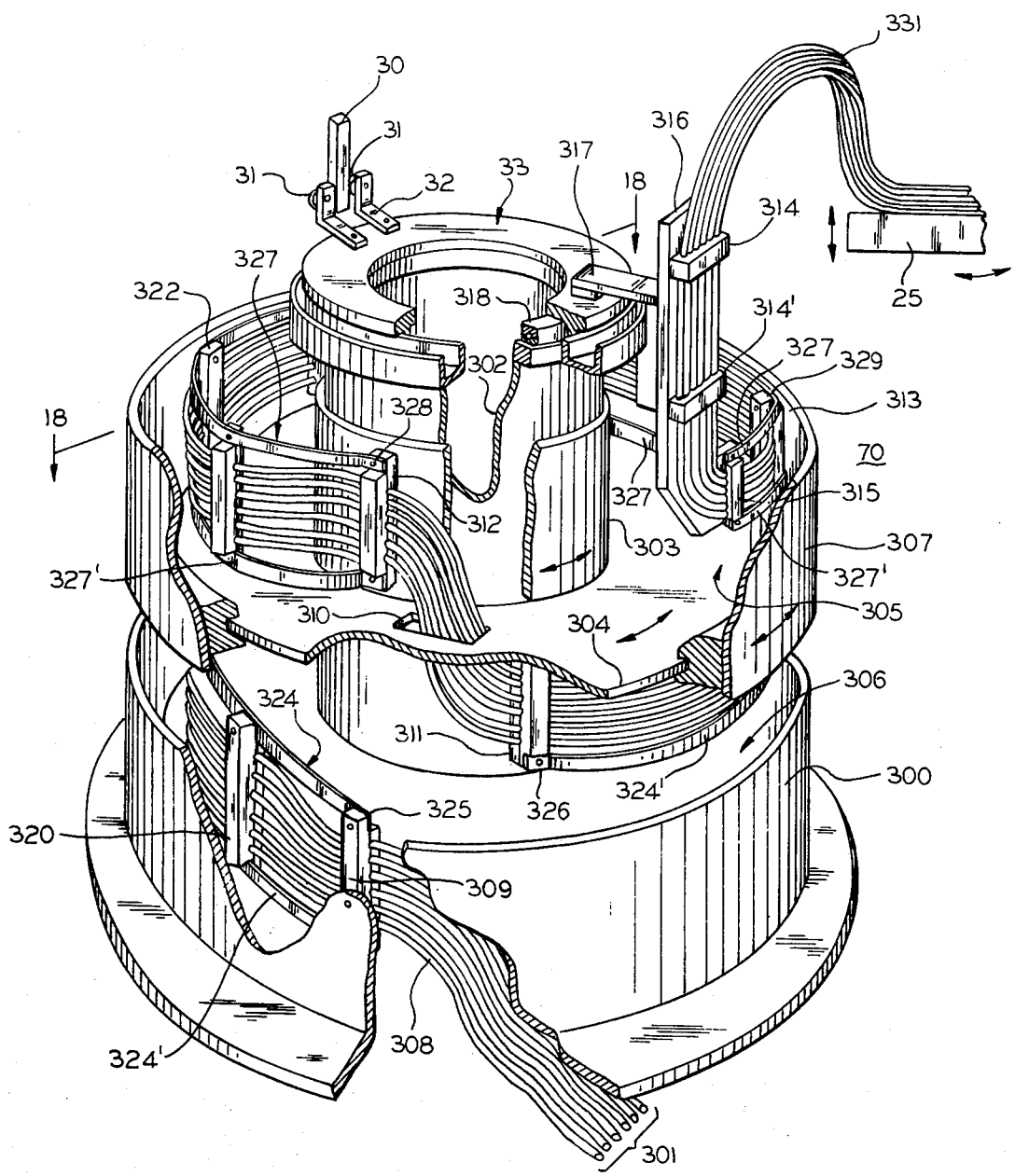
FIG. 12 is an isolated somewhat schematic view of the cable take-up mechanism with parts broken away and with the cables in an unwound state.

The cable take-up device is shown diagrammatically in FIG. 12. It comprises a stationary cylindrical base 300 through the periphery of which the group of cables 301 enter tangentially. The device has a central stationary cylindrical element 302. An idler cylinder 303 is concentric with cylinder 302 and turns freely on it. A radially extending plate 304 is fastened to idler 303. Plate 304 divides the device into an upper toroidal cavity 305 and a lower toroidal cavity 306. Plate 304 is engaged with an outer and upper cylindrical wall 307.

In FIG. 12, the starting end 308 of cable group 301 passes through a suitable opening in the wall of stationary cylinder 300 and the cables are held by a clamp 309. Clamp 309 is fastened to the interior of cylinder 300 immediately after the cable group enters. From clamp 309, the cable group makes a spiral turn in lower cavity 306 and it passes upwardly through a hole 310 in plate 304 and into upper cavity 305. Before passing upwardly, the cable group is clamped to idler 303 by a clamp 311. After passing through hole 310, the cable group is clamped with a clamp 312 to idler 303 in the upper cavity 305. Following clamp 312, the cable makes a spiral turn and reaches a clamp 313 which is one of several that assists in keeping the cables in an orderly parallel group but is not fixed to any cylinder. The cable group is then bent upwardly and helf in a pair of clamps 314, 314' and 315 which are on a bracket 316. An arm 317 extends from bracket 316. Arm 317 is fastened to a bearing annulus 33 which is also symbolized in FIG. 1 as supporting outer water container 18 for rotation. The annulus 33 is on a bearing 318 which journals it relative to central stationary cylinder 302. The annulus and bearing structure are shown in actual form in FIG. 18 which will be discussed later. In FIG. 12, annulus 33 has bracket 32 and a pair of ball bearings 31. The annulus is turned about a vertical axis by means of bearings 31 being urged rotationally by post 30 which was mentioned briefly in the discussion of FIG. 1. Recall that the post 30 is fastened to scanner arm or rotor 25 and orbits with it. Since the rotor 25 also moves up and down by virtue of being supported on elevator 39, annulus 33 will turn under the influence or orbiting post 30 but will not move vertically. Rotation of annulus 33 coordinately with rotation of scanner arm 25 causes the spiral cable groups in upper and lower cavities 305 and 306 to wind and unwind together. With a full 1½ revolutions of the rotor 25 the rotor exit cable clamps 314, 314' and 315 will rotate the full 1½ revolutions, clamp 312 and idler cylinder 303 will revolve approximately three-fourths of a revolution and clamp 325 at cable entry will remain stationary. Thus, the cable spirals in both upper and lower cavities 305 and 306 each wind and unwind approximately three-fourths turn in this embodiment.

Periodically along the cable group, additional clamps such as 320, 321 and 322 are provided. These clamps merely hold the cables in parallelism with the neutral bending axis of each cable disposed vertically relative to each other, to assure proper alignment when being as a group. They do not fasten to anything but the cables and some spring metal bands which are described in the next paragraph.

Running from clamp to clamp along with the cables in the lower cavity 306 are parallel upper and lower spring metal bands 324 and 324' which are fastened to several spaced apart clamps such as 320 and 322. Bands 324 and 324' have corresponding one ends fastened to upper and lower ends of stationary clamp 309 at 325 for example. The bands spiral around the lower cavity 306 and their other ends fasten to the upper and lower ends of clamp 311 at 326. As mentioned earlier, clamp 311 is fastened to idler cylinder 303.

The cable group in upper cavity 305 also has upper and lower spring metal supporting bands 327 and 327'. One of their corresponding ends 328 are fastened to clamp 312 which is also fixed on idler 303. The other ends 329 of bands 327 and 327' are also fixed to the last clamp 315 in upper cavity 305.

Figure 14:
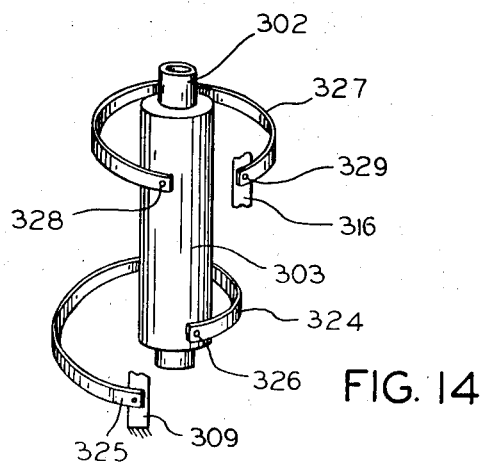
FIG. 14 is a schematic diagram of cable supporting spiral springs and the idler which are used in take-up mechanism shown in FIGS. 12, 13 and 15.

FIG. 14 shows diagrammatically, one of the two spring bands 324 from the lower cavity and 327 from the upper cavity for the purpose of showing the relationship of the bands more clearly. The outer end 325 of typical lower spring band 324 is effectively fastened to the inside of outer stationary cylindrical wall 306. The inner end 326 is fastened to idler cylinder 303 as shown. The typical upper spring band 327 has its inner end fastened to idler cylinder 303 and its outer end 329 fastened to clamp 315 and effectively to bracket 316. Looking at FIG. 14 from the top, and considering the lower spring band 324, one may see that it spirals clockwise from fixed point 325 to point 326 on the inner cylinder. Again viewing from the top, the upper spring band 327 is fastened at 328 and spirals clockwise to its free end 329. Thus, spiral spring band pairs 324 and 327 in the actual structure are unwound or open when the scan arm 25, which effectively swings end 329, is maximum counterclockwise.

When the scan arm 25 is rotated toward its clockwise limit or rotation, end 329 of band 327 moves clockwise as viewed from the top. It passes point 328 on the idler 303 radially outwardly therefrom as the coil winds. Thus, it will be seen that the upper spring band outer portion winds around the inner portion as it tightens due to clockwise rotation. At the same time, idler 303 is driven and it pulls the inner end 326 of lower spring band 324 around with it in a clockwise direction, thus tightening the lower band from the inside to the outside.

Figure 13:
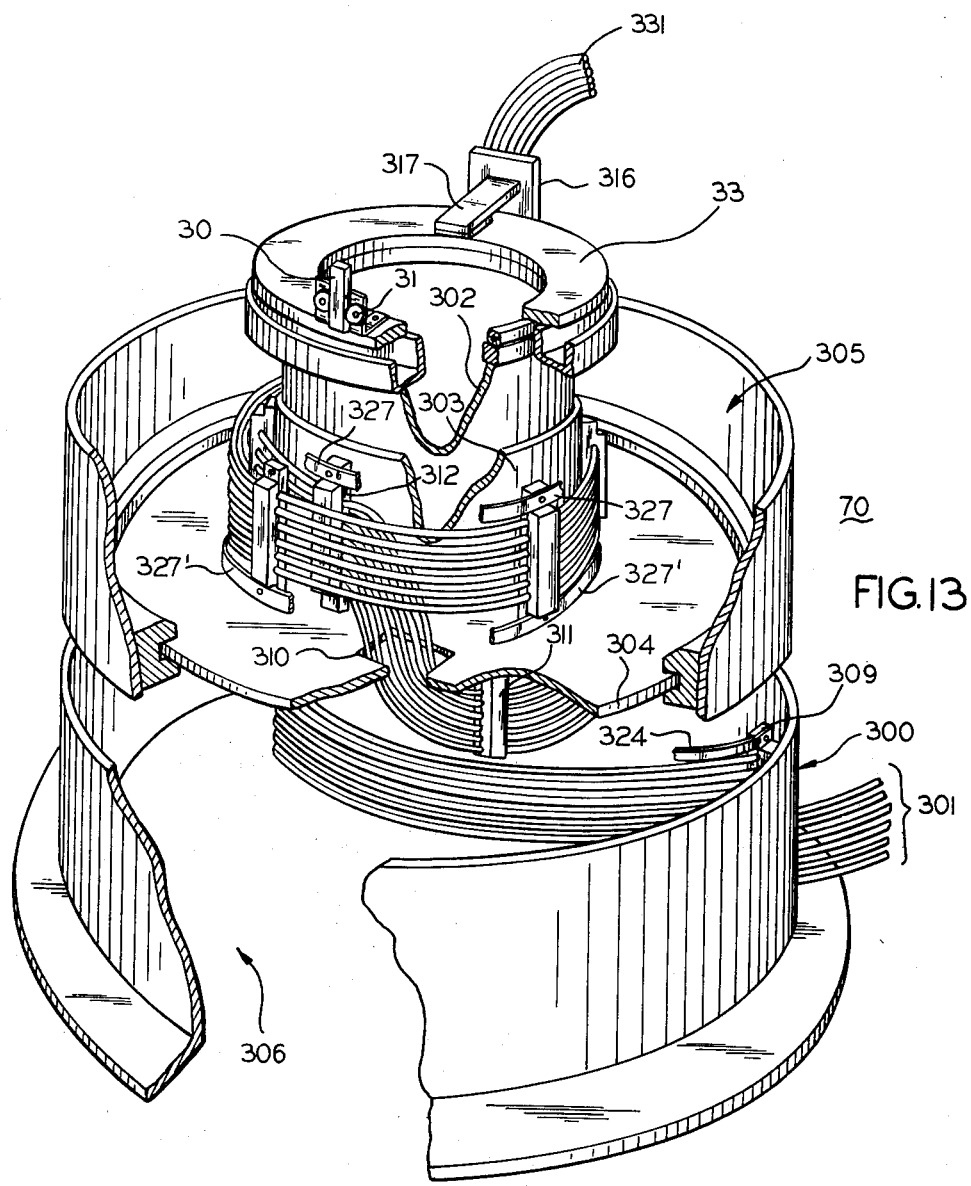
FIG. 13 is similar to FIG. 6 except that the cables are shown in a wound state.

FIG. 12 corresponds with maximum counterclockwise rotation of the scan arm where the cable loops in the upper and lower cavities 305 and 306 are unwound or open. FIG. 13 shows the cable take-up device as it appears when the scan arm or rotor 25 is turned to its maximum clockwise position. In the latter case, it will be seen that the cable in the upper and lower cavities 305 and 306 is more tightly wound. Structurally, FIGS. 12 and 13 are the same buth FIG. 13 is shown rotated 90° relative to FIG. 12 in order to be able to show the position of a cable groups more clearly when the cables are wound tight. It should be noted that the spring bands 324 and 327 are relatively thin but wide to gain flexibility and yet obtain sufficient rigidity to maintain the cables in upper and lower spirals that lie in single planes. The spring band spirals have spaced holes for assembling them to the clamps and to assure proper spacing of the clamps.

In FIG. 12, a fragment of the scan arm or rotor 25 is shown in the upper right. A pair of arrows are placed next to this fragment to suggest that it rotates and elevates. Rotation displacement compensation for the cables has been described. Compensation for the changing elevation of the rotor 25 is obtained by forming the outer end of the cable with a free loop 331 as can be seen particularly well in FIG. 12.

Some characteristics of the spring band cable take-up system which have been casually mentioned heretofore will now be recapitulated and some other characteristics which may not have been recognized will not be elucidated. Observe, for instance, that the pairs of spring bands such as 324 and 324' and 327 and 327' have their neutral bending axis as close as possible to being coincident vertically or over and under the neutral bending axes of the cables in each group. This contributes to avoiding stresses which would be manifested as undue stiffness of the cable and spring combination in the horizontal plane which would result undesirably in more torsional force being required to wind and unwind the cables spirally. Even though good flexibility of the cables and springs is achieved in planes along which they bend, the springs still exhibit stiffness in a direction normal to the bending planes such as to limit sagging of the cables vertically. Although not possible to depict, the spring bands are preformed before being assembled to the cable groups. Unless the bands are preformed at the inner end region, the bands will tend to press outwardly, as will the cables, and create friction between them when unwinding. A uniform spiral spring having a shape conforming with the mathematical equation for a spiral which would have its outer end fixed to a stationary element and its inner end fastened to a rotatable element such as idler 302 will, when being wound tighter, have its inner end region tend to take on a sharper radius or tighten sooner toward the idler while its outer part is still more open or radially expanded. This too results in frictional drag and nonuniform torque. And as stated earlier, the drag is perhaps more consequential when unwinding. In accordance with the invention, the spring bands are preformed with a long radius curvature from its outer end toward the inner end and as a portion near the inner end is reached the radius of curvature is reduced considerably. Then when the spring band is formed as a spiral approximately with its ends attached and with the parts between the ends clamped to the cables, the bands will have the shape needed for unwinding properly, that is, without having adjacent inside turns dragging against each other. With uniform winding and unwinding and proper contour of the cables being achieved and maintained in this way, the cables are not bent sharply at any time so overstressing them is avoided and frictional wear and binding of the cables or any other supported flexible element in the group is avoided.

Figure 15:
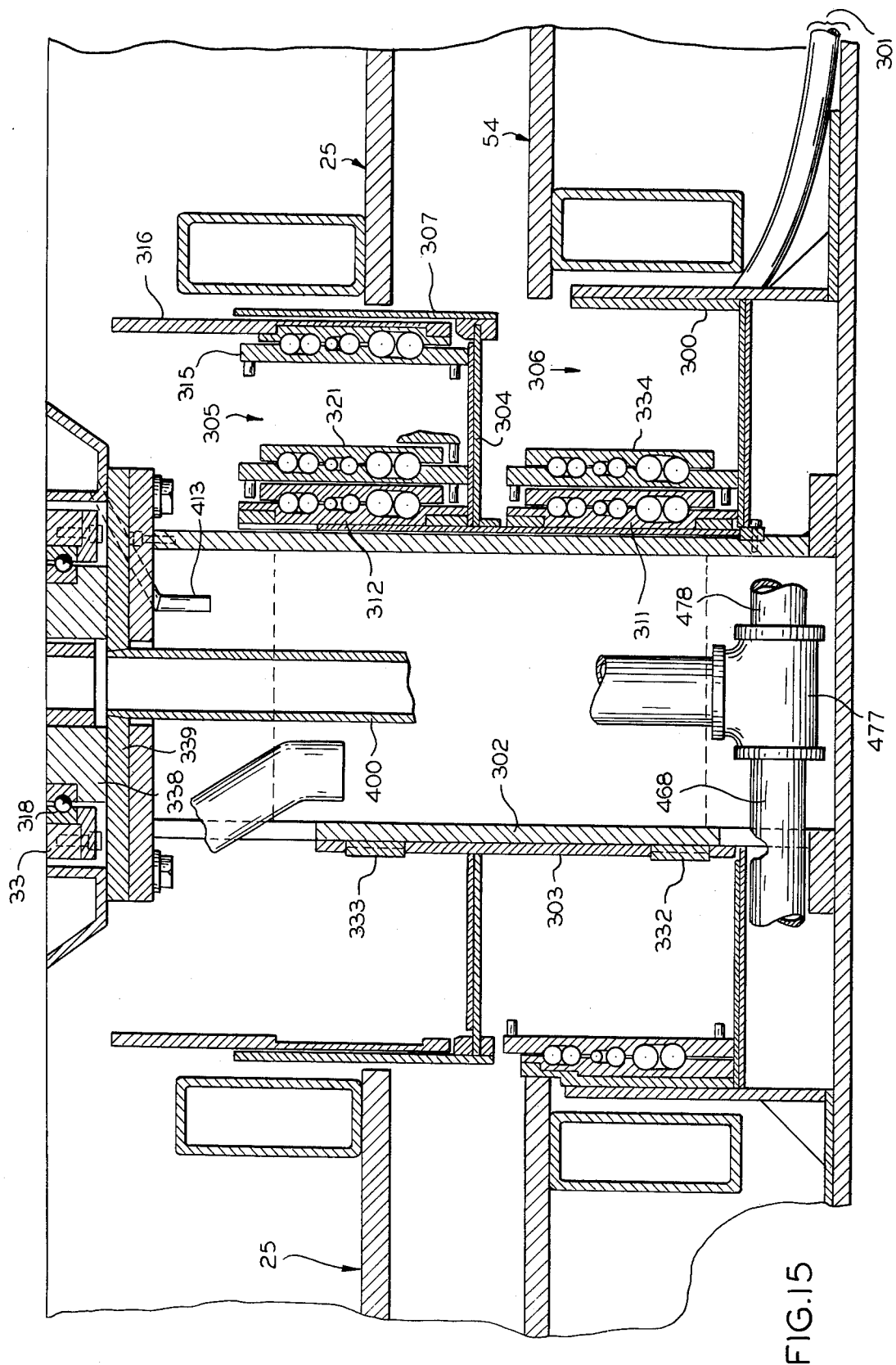
FIG. 15 is a partial vertical section of the actual cable take-up mechanism which is taken along the vertical plane 15—15 of the schematically represented apparatus in FIG. 1.

A vertical section showing the actual construction of the cable take-up device appears in FIG. 15. In this Figure, parts corresponding with those in FIGS. 12–14 are given the same reference numerals. The free wheeling idler cylinder 303 is seen to be concentric with stationary inner cylinder 302. Idler cylinder has several circumferentially spaced bearing inserts such as 332 and 333. These inserts may be a low friction material such as Delrin or nylon. Insider cable clamp 311 in lower cavity 306 is shown fastened to idler cylinder 303. The other cable clamps or holders such as 321 in the upper cavity 305 or 334 in the lower cavity winds and unwinds. A fragment of the rotatable and vertically movable scan arm 25 is marked with the same reference number as in FIG. 12.

Figure 18:
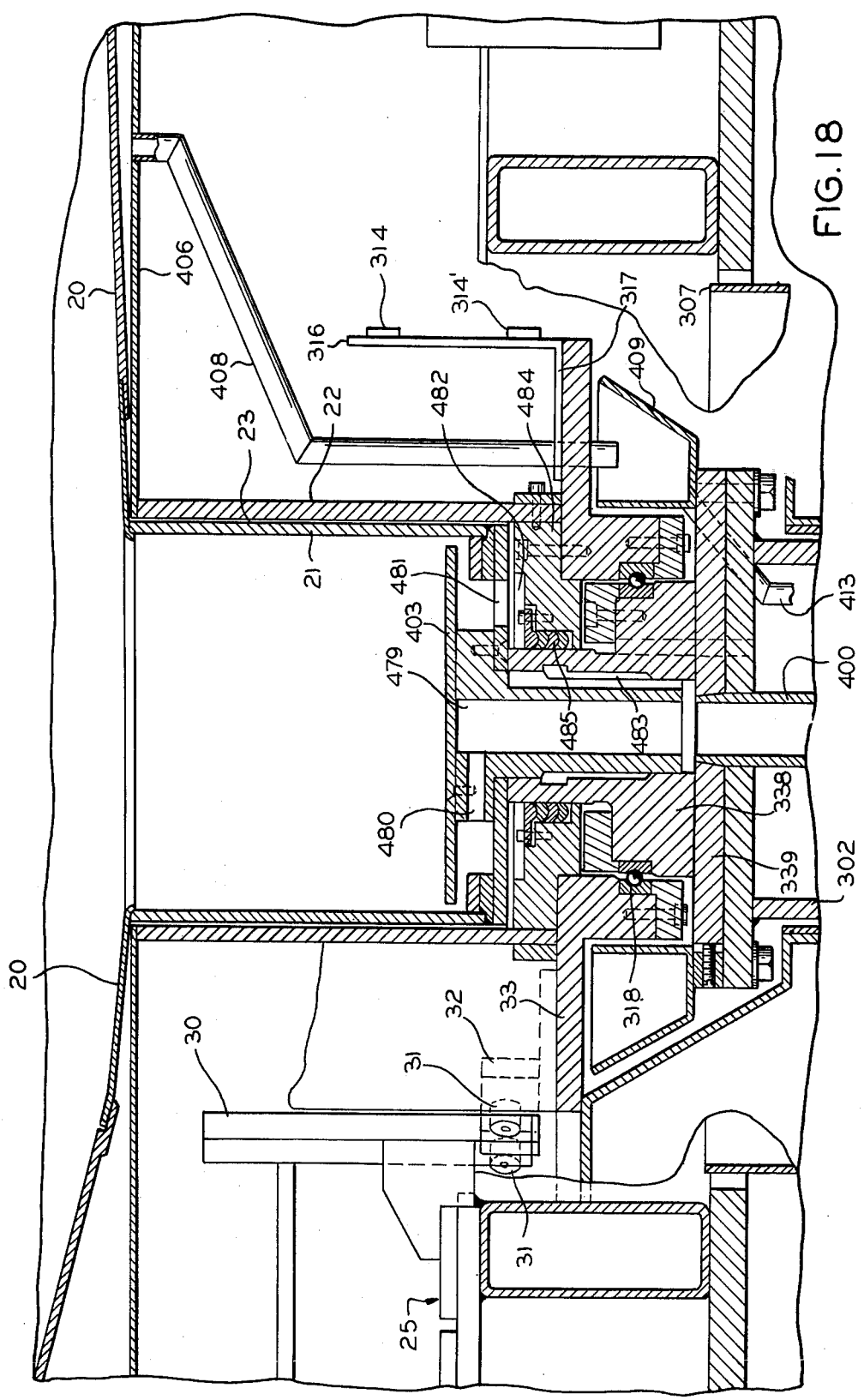
FIG. 18 is a fragmentary vertical section of the actual apparatus taken along the vertical plane 18—18 of the schematically represented apparatus in FIG. 1 and showing of the construction of the inner and outer water chambers, the means for rotating the outer chamber and part of the scanner rotor.

FIG. 18 shows a partial vertical section, corresponding roughly with the vertical plane 18—18 in FIG. 12, to illustrate how the cable take-up device is driven in an actual embodiment. At the left, a portion of the rotating scanner arm is marked 25, and, it will be understood that it is on the elevator 39 which moves down in increments during a scan. The drive post 30, heretofore discussed on the basis of a symbolic showing, is fastened to the rotor or scanner arm 25. Post 30 is, of course, vertically movable with the rotor which is on the elevator. The orbit post drives member 33, which was called an annulus in connection with FIG. 12, rotationally on a ball bearing 318. Ball bearing 318 is also shown in FIGS. 12 and 13. The orbiting post 30 drives annulus 33 by means of rollers 31 on bracket 32. The rollers 31 bear on the post and engage the post between them to effect the vertical sliding connection. The inner face of bearing 318 is fixed on a member 338 which is, in turn, fastened to a platform 339 which rests on stationary inner cylinder 302. In FIG. 18, the bracket which supports the cable at its upper end leading to loop 331 is again marked 316 and its associated cable clamps are again marked 314 and 314'. One may also see in FIG. 18 that outer water container 22 will rotate with annulus 33 on which it is mounted but the container will not change its elevation. Other components shown in FIG. 18 will be identified and discussed later in connection with the describing water system.

Figure 16:
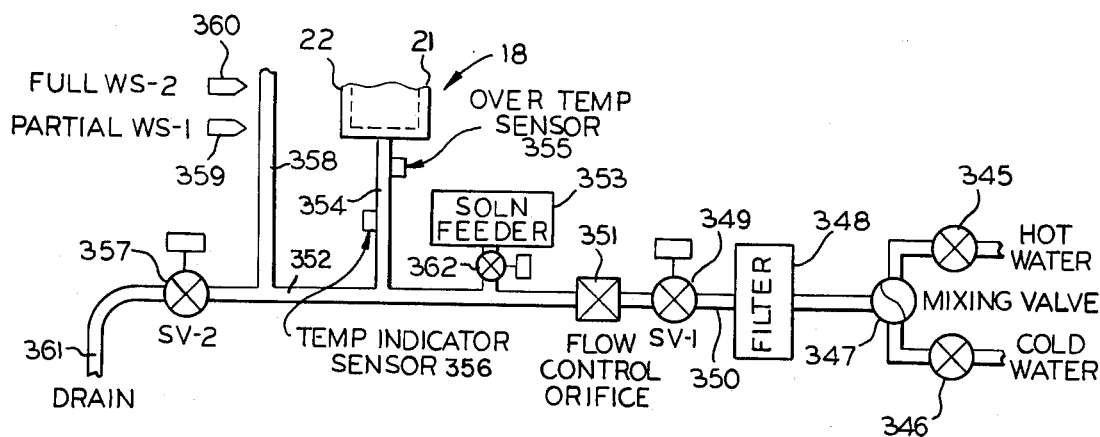
FIG. 16 is a schematic diagram of the components of a basic water supply system used in the apparatus.

Refer now to FIG. 16 for a discussion of the water system. During a breast examination, inner breast container 21 and outer water container 22 are both filled with water in this embodiment. The water used in the containers is controlled at a temperature that is comfortable to the subject. A surfactant is also used in the water so that it wets the patient's skin and minimizes surface bubbles. Bubbles should be removed to avoid adverse effects on detected signals. Germicides and fungicides may also be added.

The components of a rudimentary water system as employed in the new apparatus is shown in FIG. 16. Basically, there are hot and cold water input valves 345 and 346 which lead to a temperature regulating mixing valve 347. Water from this valve passes through a filter 348 in the feed line 350. There is a solenoid controlled valve 349 in the feed line 350. Flow rate is controlled or established by a controlled orifice valve 351. Surfactants, fungicide and germicide in solution are fed into the water line 352 from a solute feeder 353. Under the control of solenoid valve 349, water is admitted to the inner breast container 21 and to the outer container 22. In contact with the water flow path to the containers, there is an over-temperature sensor 355 and a temperature indication sensor 356. When it is desired to fill containers 21 and 22 partially or completely, a solenoid controlled drain valve marked 357 and SV-2 is automatically closed. This causes the water level to rise in a slight glass 358 which has two sensors associated with it. One sensor 359 or WS-1 indicates when container 21 is partially filled to a predetermined level. Another sensor 360 or WS-2 indicates when the container is completely filled. Solenoid valve 357 is opened when it is desired to drain the system through a drain line 361. Solution is fed from feeder 353 under the control of a solenoid valve 362 only when fresh water is injected into the system through orifice valve 351.

Figure 17:
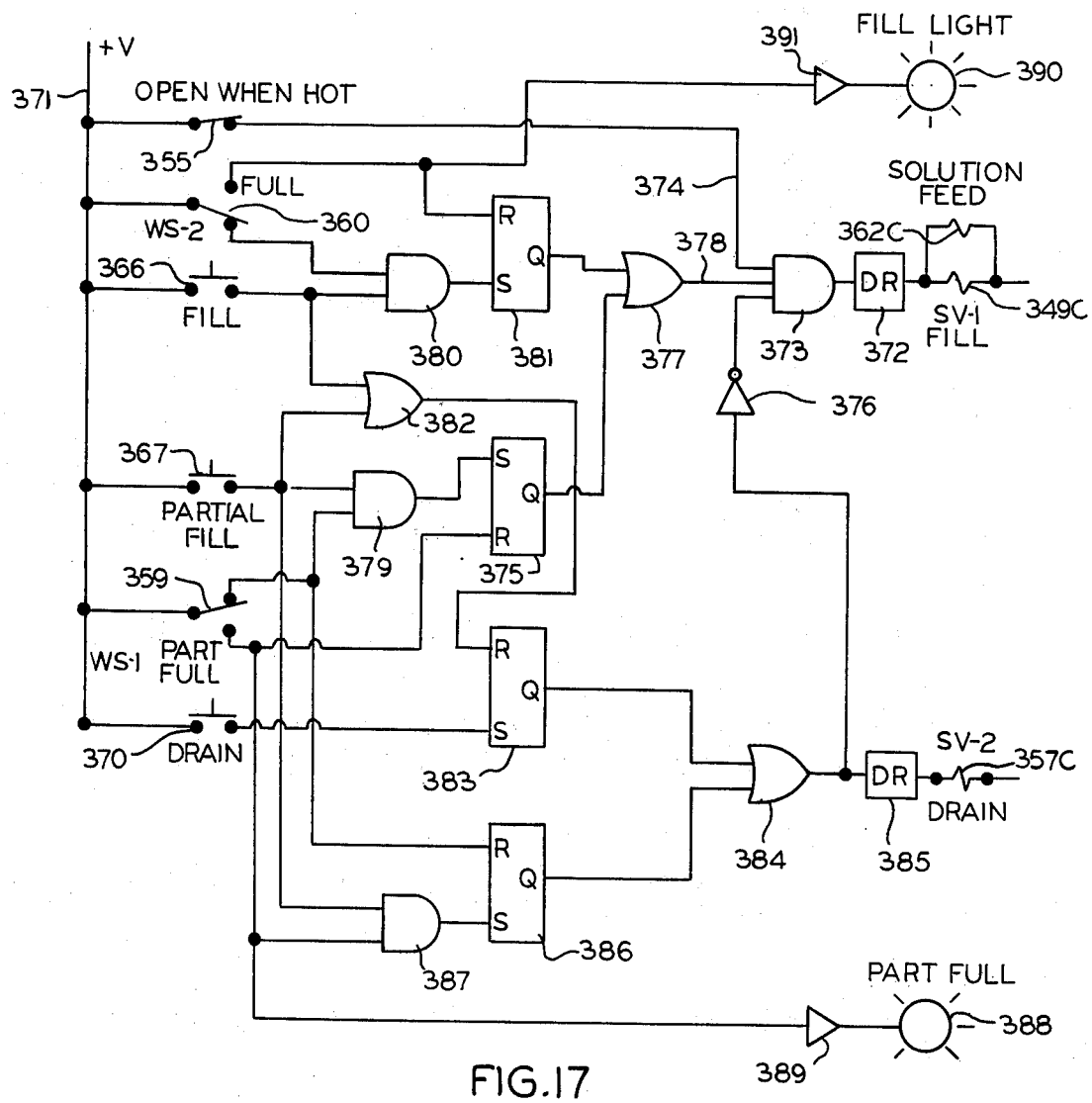
FIG. 17 is a diagram of the logic circuitry for controlling the water system of the apparatus.

The logic system for controlling the water used in the apparatus is shown schematically in FIG. 17. It has several switches, some manually and some automatically operated, which are supplied from a logic voltage bus 371. The switches can be variously operated to selectively partially fill, completely fill and drain water container 21.

The operating coils for the principal solenoid valves in FIG. 16 are designated by the same number in FIG. 17 with a suffix "C" added to indicate the coil.

When filling or partialy filling of the system is commanded, solenoid valve coil 349C in FIG. 17 is energized and valve 349 in FIG. 16 is opened. At the same time, solution feed control valve 362C in FIG. 17 is energized and solenoid valve 362 in FIG. 16 is opened. The coil 357C in FIG. 17 is energized to open valve 357 in FIG. 16 when draining the system is commanded. The logic is such that draining is inhibited when either fill or partial fill are commanded and until draining is commanded.

Coils 362C and 349C for solution feed and filling are driven through an optically coupled isolator driver 372 which is in the output line of an AND gate 373. The AND gate has three inputs. One input 374 has the overtemperature sensor switch contacts 355 in the series with it. This is primarily a safety switch since water temperature is regulated by mixing valve 347. However, if the water temperature exceeds the comfort level, switch 355 opens and AND gate 373 is disabled so water and solution cannot be fed.

Hereafter in reference to FIG. 17, structure and function will be described concurrently.

When setting up a patient for an examination, and before the breast is admitted to container 21, it is desirable to fill the container partially so there will be no overflow due to the breast entering. Partial fill is initiated by manually operating push button switch 367. This supplies one input to an AND gate 374. The other input to the AND gate is supplied by the two-position partial full indicating switch 359 which, when the container is partially filled is in the position in which it is shown in FIG. 17. Thus, both inputs to AND gate 374 go high and its output is high. This sets a flip-flop 375 and causes its Q output to go high. When Q output of flip-flop 375 goes high, it causes the output 378 of an OR gate 377 to go high. The output of OR gate 377 is another input 375 to AND gate 373. At this juncture, inputs 374 and 375 to AND gate 373 are high and, as long as a command to drain the system is not given, the other input 376 to AND gate 373 will be high. Thus, the output of AND gate 373 will be high and fill coil 349C and solution feed coil 362C will be energized so as to start partial fill of the breast container with water. When the predetermined partial fill level has been reached, the contact of switch 359 transfers and provides a logic signal to the reset terminal R of flip-flop 375. Its Q output then goes low as does the input to OR gate 377. This causes the output of AND gate 373 to go low and deenergize the solution feed and fill relay coils 362C and 349C.

When the patient is in place and it is desired to fill water container 21, a fill push button switch 366 is operated. It provides one input to AND gate 380. The other input to the AND gate is through the full indicating switch 360 which has one closed circuit as shown when the container is not filled yet. Thus, both inputs to AND gate 380 are high as is its output. This sets a flip-flop 381 and its Q output goes high. This constitutes another input to OR gate 377 and again contributes to making all inputs to AND gate 373 high so that solenoid valve coils 362C and 349C will be energized. When container 21 becomes filled, switch 360 transfers its contacts so as to put a high signal on the reset terminal R of flip-flop 381, thus making its Q output go low. The output of OR gate 377, therefore, goes low and so does the output of AND gate 373. When the latter happens, coils 362C and 349C are deenergized and filling stops.

When either fill push button switch 366 or partial fill switch 367 is depressed, a high signal is supplied to one or the other inputs of an OR gate 382. This causes the output of gate 382 to go high and apply a reset signal to a flip-flop 383. The Q output of this flip-flop then goes low and provides a low signal to one input of an OR gate 384. In the absence of a high signal on the other input of this OR gate, a driver 385 will be deenergized so it cannot supply a driving voltage to the drain valve solenoid 357C, thus keeping the valve 357 closed.

Another input to OR gate 384 is from the Q output of a flip-flop 386 which has a set input, S, and a reset input, R. The set input is supplied from the output of an AND gate 387. This AND gate has two inputs. One input goes high when the container is at the partial fill level which causes switch 359 to transfer. Now, if the manual push button switch 367 for partial filling is operated, both inputs of AND gate 387 will go high as will the Q output of flip-flop 386 and the output of OR gate 384. This will cause the drain solenoid 357C to energize and prevent filling the container 21 above partial fill.

To drain the system completely, manual push button 370 is depressed. This applies a high input to the set terminal of flip-flop 383, thus causing its Q output to go high. This results in the output of OR gate 384 going high and with inversion in driver 385 causes drain valve solenoid 357C to be deenergized so the valve will open and the system can drain.

A signal lamp 388 is provided for indicating when the water in container 21 has reached the predetermined partial fill level. The lamp is supplied with operating voltage through a buffer 389 which receives logic signals from the one terminal of partial fill responsive switch 359. Lamp 388 is only energized when the contact of partial fill indicating switch 359 is transferred from the position in which it is shown.

A signal lamp 390 is provided to signal the operator when the container 21 is completely filled as commanded. Lamp 390 has a buffer 391 driving it and the buffer is controlled by a logic signal from one of the contacts of full indicating switch 360. This contact transfers from the position in which it is shown when the level of fluid in container 21 reaches the full level.

FIG. 9 is a functional diagram of a more advanced version of a water system for use in the breast scanner. This system conditions the water which comes into contact with the patient in respect to cleanliness, temperature and wettability. It provides for addition of a surfactant and, if desired, a germicide and a fungicide to the water. The surfactant reduces normal surface tension of the water to minimize the possibility of formation of air bubbles which could cling to the walls of the water containers or to the immersed breast and cause erroneous x-ray absorption indications. The system also provides for exposing the water to vacuum to remove some of the dissolved air to further enhance wetting and good water contact with the patient's breast and the inner and outer water containers and to eliminate air bubbles. The system has a storage tank for holding conditioned water in readiness for use at all times. It assures isolation of the patient from the untreated water and water that is used for a prior patient. Provision is made for constant water overflow at the top of the water containers, at a substantially reduced rate, to conserve conditioned water and yet assure the presence of water at the top scan layer. The water system is designed to maximize the number of patients that can be examined with the apparatus by minimizing the waiting time for the water conditioning system to complete its cycle prior to use of the conditioned water to refill the water containers.

In this system, a partial water level control is provided which permits the operator to initiate filling of the inner and outer water containers at any time prior to immersing the breast. After the operator initiates the filling operation, the filling action is automatic and stops at an optimum level in the water containers short of completely filling them. This avoids having water overflow when the patient's breast is immersed. After final patient immersion and positioning, the operator initiates a second control which completes the final fill operation, following which a continuous limited rate overflow is allowed to occur. When examination of one breast is complete and before transferring the patient into a position for examination of the other breast, actuation by the operator of a partial level control permits water to drain only to a partial level, rather than completely draining, thus conserving the supply of conditioned water. This operating mode provides greater patient comfort and removes the possibility of some slight water overflow into the patient support if the containers were not permtted to partially drain before immersing the second breast for examination.

A further feature of the more sophisticated system is that the water fill rate below the partial level is fast, while the water is supplied at a slow fill rate when it has gone above this partial level.

Means are also provided for maintaining the water that comes in contact with the patient at a comfortable temperature level.

In the FIG. 19 diagram, the x-ray transparent inner water container is marked 21 as it is in the other FIGURES. The outer x-ray transparent container is marked 22. A combination feed and drain line 400 is shown symbolically as being connected to the outer container but there is an opening 401 in the inner container and a passageway 402 to the outer container which places these containers in communication with dual purpose drain and fill pipe line 400. Within inner breast container 21 there is a diffuser or distributor 403 which deflects the water to the walls of the container and reduces agitation during filling. Maximum fill level is indicated by the dashed line marked 404. Partial fill is indicated by the dashed line marked 416. The inner container 21 is shown as flaring outwardly and upwardly at 405 and the outer container 22 is shown as flaring similarly at 406. Interconnection of the inner and outer containers at their tops is indicated by a small gap marked 407. Also connected to the flared out portion or upper pan 406 which communicates with both containers is an overflow drain pipe 408 leading to annular pan 409 which also shows in FIG. 18.

The partial fill level 416 and the complete fill level 404 of the container 21 and 22 is ascertained using a sight glass tube 417 which connects to the bottoms of the containers via drain line 400. Water will rise in glass tube 417 in correspondence with the level in the containers. There is a light source such as a light emitting diode (LED) 418 on one side of the tube and a sensor such as light responsive diode or transistor WSS-1 in line with it on the other side of the tube and at the partial fill level 416. Diode WSS-1 changes its output signal when the water rises to the level in the tube 417 corresponding with 416. Thus, the output signal change can be used to terminate the water feed at partial fill level 416.

Another LED 419 is provided on one side of the sight tube 417 with another light sensitive diode or transistor WSS-2 at the same level diametrically opposite. Sensor WSS-2 is at a level corresponding with full fill level 404 in the containers 21 and 22 and responds to water intervening in the sight glass by changings its output signal. Thus, this signal change can be used to terminate water feed when the containers are completely filled to level 404.

In the lower left of FIG. 19 one may see that the water inputs to the system comprise a hot water feed line 420 and a cold water feed line 421. The hot water line has a manually controlled valve 422 and the cold water line has a similar valve 423. These valves feed a mixing valve assembly marked MXV. The mixing valve is conventional and has a symbolically shown component 425 for preliminary regulation of the temperature of the mixed water. It also has a pressure regulator valve 426. Discharge of the mixed warm water is through a manually controlled valve 427 which leads to a filter 428. Connected in series with the filter is a solenoid valve SSV-1 which is in series with a manual throttle or feed control valve marked FCV-1. The flow paths and devices thus far described regulate flow into a storage tank 431 preparatory to conditioning the water within this tank. Solenoid valve SSV-1 in the tank input line is for turning off the water supply to storage tank 431 automatically as is required in connection with the automatic operating mode of the system. Feed control valve FCV-1 is for regulating the flow rate to tank 431.

The capacity of storage tank 431 is preferably at least great enough to keep available sufficient conditioned water for examining a single patient. The tank is provided with an electric heater 432 which is controlled so as to maintain the temperature of the water in tanke 413 at about 90° F. The tank has an upper temperature limit sensor marked TS-1 which is involved in prohibiting feeding of water into the breast container 21 if the temperature is so high as to be unsafe or uncomfortable to the patient. Another temperature sensor TS-2 is located in tank 431 and it provides a ready signal if water temperature is proper for use in the breast container, that is, within about 3° F above or below 90° F.

Also located in storage tank 431 are water level sensors and controls marked WLC-1 and WLC-1A. The level sensors limit water supply to the tank by controlling operation of solenoid valve SSV-1. Electric contacts in float operated switch assembly WLC-1 are operated when a first desired high water level is attained in the tank 431. In such case, solenoid valve SSV-1 is caused to close. WLC-1A responds to the water level in the tank having reached an emergency upper level limit in which casey a 3-way solenoid operated valve SV-5, is actuated. Upon such event, overflow water from the tank 431 flows through a discharge pipe 441 and through valve SV-5 which has a drain line 442 connected to one of its outlet ports. Drain line 442 discharges into a collector 443 which has a drain line 444 leading from it to a main drain line 445. Tank 431 may be drained completely when desired by opening a manually controlled valve 446 which permits discharge through a pipe 447 to collector 443.

Tank 431 also has a float operated switch assembly or sensor WLC-2 sensing a low water level limit. The low water level limit is indicated by the dashed line 449 and the normal fill level is indicated by the line 450.

Under certain circumstances in the operating mode of the system, the water in storage tank 431 may be subjected to vacuum created by a vacuum pump 455 which connects to tank 431 through 3-way solenoid operated valve SV-5. Under certain circumstances, such as where the water is being conditioned before it is delivered to breast container 21, vacuum pump 455 is turned on and solenoid valve 440 is actuated to a position where tank 431 may be evacuated so as to remove dissolved air from the water. The line leading from tank 431 to the vacuum pump preferably has a trap or demister 456 for removal of water particles, but not vapor, before the air which is deaerated reaches the vacuum pump.

A solution of water conditioning additives may be fed to the water in storage tank 431 from a reservoir 457 controlled by a solenoid valve marked SF. Valve SF is only open during the filling or refilling of the tank, thus metering in the proper proportion of additives to correspond to the amount of water added to or replaced in the conditioning tank 431.

Conditioned water is delivered from conditioned water tank 431 to inner and outer breast containers 21 and 22 by means of a pump 460 that is driven by a variable speed motor 464. This pump has a manually controlled valve 461 in its input line 462. Valve 461 is merely for service purposes. Pump 460 is adapted for fast and slow delivery rates to its output line 463. The delivery rates are a function of the speed of pump drive motor 464. The system as presently devised calls for running the pump at one of two speeds. There are two discharge paths for the output from pump 460. One is through a line 465 in which there is a solenoid valve marked SSV-3. The discharge from valve SSV-3 is through pipes 467 and 468 which lead to multi-purpose drain and fill pipe 400. The other discharge path for pump 460 is through a line 469 in which there is a manually controllable overflow rate feed control valve FCV-2. In line 469 there is also a solenoid operated 3-way valve which is marked SSV-2. Three-way valve SSV-2 has one normally open port leading to a recirculation line 472. It will be evident that during the water conditioning cycle, solenoid valve SSV-3 should be closed and the port of solenoid valve SSV-2 leading to recirculation line 472 should be open so that the water stored in tank 431 may be constantly recirculated for mixing purposes. Vacuum is drawn on the storage tank with vacuum pump 455 while water pump 460 is recirculating the water. Vacuum is released before water is fed into the breast container 21. When the system is simply operating in its recirculating mode, no water flows through overflow feed control valve FCV-2 by virtue of the way in which solenoid valve SSV-2 is actuated.

When an adequate quantity of water for a single patient has been conditioned in tank 431 insofar as additives, dearation and temperature conditions are concerned, interlocks, not shown, function to permit introduction of water into containers 21 and 22. Control circuitry and suitable manually operated control switches, not shown in FIG. 19, are used for initiating feed of water to inner and outer containers 21 and 22. When the signal for a partial fill is given, solenoid valve SSV-2 is actuated to prevent recirculation through line 472 and solenoid valve SSV-3 is actuated open. At this time, pump 460 is operated at its high rate so as to bring about fast fill of the containers 21 and 22 through solenoid valve SSV-3. When the water in containers 21 and 22 reaches the partial fill level, solenoid valve SSV-3 closes and solenoid valve SSV-2 transfers so that pump 460 operates in its recirculating mode. When container 21 is partially filled as just described, a breast of the patient may be immersed in the container. When the patient is deemed to be properly set up for examination, the operator effectuates complete filling of containers 21 and 22. Upon this event, solenoid valve SSV-3 opens again, recirculation through line 472 is inhibited and pump 460 is transferred to its low speed or slow fill rate mode. When final filling of the containers 21 and 22 at the slow rate is completed, water overlows into drain line 408 and into drain pan 409. Sensor WWS-2 senses this condition and responds by closing solenoid valve SSV-3. Pump 460 now delivers water at a greatly reduced flow rate through feed control valve FCV-2 to containers 21 and 22.

The main drain line 400 and series connected portion 445 has a solenoid valve SV-4 in it. When an x-ray scan series is completed for the first breast of a patient, the operator has the option of draining the inner and outer containers 21 and 22 partially whereby solenoid valve SV-4 opens until sensor WSS-1 on the sight glass 417 for the senses that the water level has been reduced to about, for example, 2 centimeters from full and then solenoid valve SV-4 closes again. For a complete drain between patients, drain valve SV-4 opens to drain the system and refilling of storage tank 431 is automatically initiated.

To recapitulate operation of the water system, a cycle is initiated by the operator. At the start, main drain valve SV-4 is closed and input feed solenoid valve SSV-1 is opened, container feed solenoid valve SSV-3 is closed, and 3-way solenoid valve SSV-2 and vacuum control valve SV-4 are deactivated. Water can then recirculate through line 472. Water is admitted to tank 431 and solenoid valve SF meters in the additive solutions until WLC-1 closes SSV-1, and SV-5 is open and pump 455 is actuated for pumping a vacuum. After pump 455 has pumped vacuum for about 5 minutes or such other time as is selected and TS-2 senses proper temperature in tank 431, and neither TS-1 nor WLC-1A have been actuated, a "water ready" indication and signal are supplied.

When the "water ready" conditions are satisfied, this condition stays in effect until TS-1 or WLC-1A is actuated or an operator controlled drain signal is given. Water will not feed to the inner and outer containers 21 and 22 unless "water ready" condition is satisfied. Upon that event, the operator initiation of "fill" control actuates solenoid valves SSV-2 and SSV-3, filling the containers 21 and 22 at the fast rate until WSS-1 causes pump 460 to transfer to its slow feed rate. When WSS-2 senses water, SSV-3 closes, with water continuing to feed through FCV-2 only at the overflow rate. Operator initiation of the partial level control causes feed at the fast rate until WSS-1 causes SSV-3 to close and to deactivate SSV-2 so as to cause the pump 460 to recirculate water in the tank 431. Continuation of the fill to above about 2 centimeters from the top of the containers 21, 22 which fill has been interrupted at partial fill level by WSS-1, is effectuated by the operator as mentioned above. During normal fill, water continues to overflow from containers 21 and 22 until a manually induced drain signal is given in which case drain valve SV-4 opens. This solenoid valve SV-4 remains open until a water feed operation is initiated by the operator inducing fill or partial fill.

The system is governed by interlocks and other protective devices. For instance, sensor TS-1 in storage tank 431 will prevent water that is too hot from being fed to the breast containers by inhibiting the water-ready condition and water feed circuits and, of course, by deenergizing water heater 342. WLC-2, the lower water level control, is involved in inhibiting heater 432 and power to water pump 460 so that the pump cannot run in a dry condition. If main supply valve SSV-1 should fail to close when the storage tank 431 is filled due to failure of water level control sensor WLC-1, or other failure, a secondary switch and sensor WLC-1A which is set for a slightly higher water level senses the condition and operates solenoid valve SV-5 to let the tank 431 drain through the normal air vent line and overflow drain 442. Secondary sensor WLC-1A also causes vacuum pump 455 to be deenergized and causes the water ready condition to be aborted.

Parts of the water flow path and the water flow piping are shown in the actual structure of the apparatus depicted in FIGS. 15 and 18. In FIG. 15, one may see the dual purpose main fill and drain pipe 400 with leads to the containers from a pipe T 477. A fragment of conditioned water feedline 468 is shown leading into the T and the drain line 478 leading to main drain solenoid valve SV-4 in FIG. 19 is shown fragmentarily.

In FIG. 18, it is evident that the main drain-feedline 400 flows into the central opening 479 and communicates with the interior of inner container 21 through several radial bores 480. The bottom of inner container 21 has an opening 481 leading to a small passage 482 which allows water to flow to the interspaced 23 between inner and outer containers 21 and 22. The central tube containing passageway 479 is keyed to bearing support 338 with keys such as 483 so the inner container cannot rotate.

As was explained in the early part of this description, outer container 22 is supported sealingly on a rotatable member 33 which is journaled to stationary member 338 by means of a ball bearing 318. Leakage is prevented between the rotatable ring 484 and stationary member 338 by means of a packed seal 485. One may see in FIG. 18 that water can rise in inner and outer containers 21 and 22 until it spills into pan 406 on the way to overflow 408. Lower annular drain pan 409 which is shown schematically in FIG. 19 and has been mentioned briefly in discussing that Figure appears more realistically in FIG. 18. It should be noted that the drain tube 408 leading from pan 406 orbits with it and it spills into stationary annular pan 409. In turn, a tube 413 leads from drain pan 409 to the inside of cylinder 302 from which water can drain.

Figure 21:
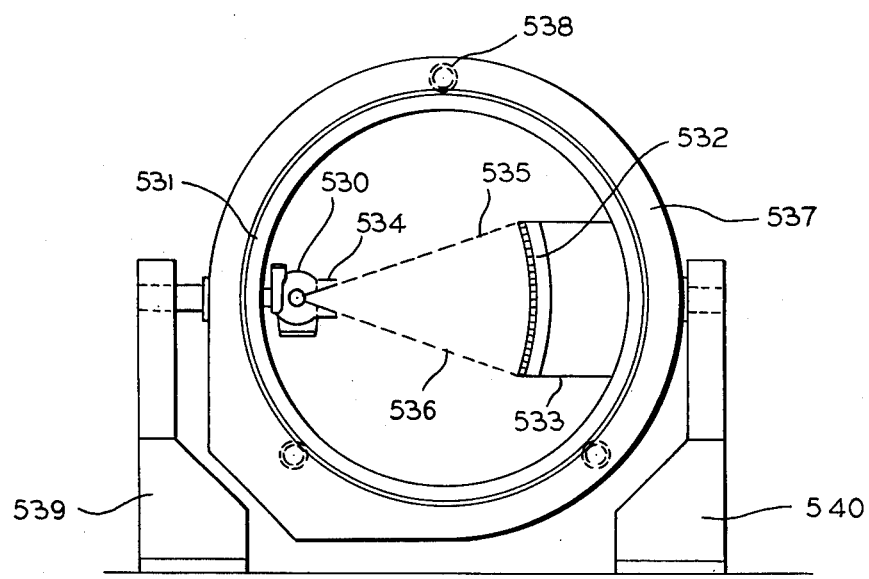
FIGS. 21 and 22 are diagrammatic front elevation and side elevation views of a whole body x-ray scanner in which several of the concepts discussed herein may be used.
Figure 22:
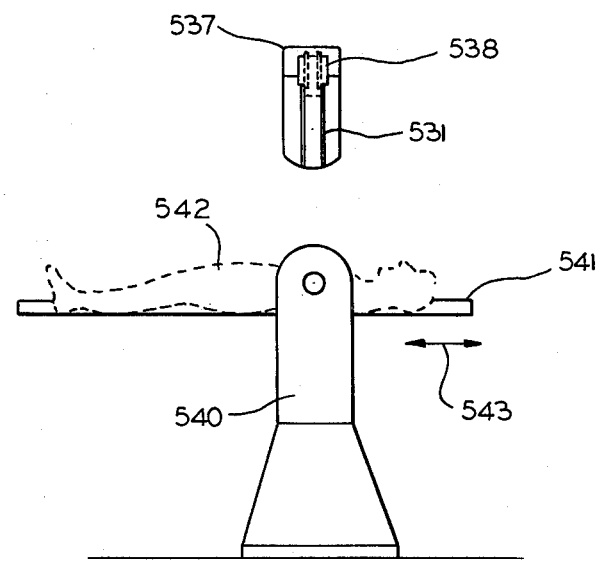

A whole body x-ray scanner in which most of the new concepts hereinbefore discussed are applicable is shown diagrammatically in FIGS. 21 and 22. The x-ray tube casing 530 is mounted on a rotatable ring 531. The multiple detector array 532 is on a support 533 which is also mounted on ring 531. The x-ray source is provided with a collimator 534 which defines the beam emanating essentially from a point source into a fan-shaped beam lying within boundaries suggested by dashed lines 535 and 536. The fan-shaped beam is collimated into a thin layer as discussed earlier. Ring 531 is mounted in a frame 537 on rollers such as 538. Thus, ring 531 is rotatable about a substantially horizontal axis such that when a patient is supported on the axis, the x-ray tube 530 and detector array 532 may orbit jointly around the patient for scanning a single layer of the body at a time. Frame 537 is mounted on columns 539 and 540. The motor drive mechanism for rotating ring 531 is not shown. Additional x-ray sources 530 and detectors 532 could be mounted on the ring 531 in which case rotational scan speed can be increased.

FIG. 22 illustrates how the body of the patient is supported on the rotational axis of ring 531. A fragmentarily shown x-ray permeable table 541 is used to support the body 542. The table is movable axially as suggested by the arrow 543.

The operating mode of the FIGS. 21 and 22 whole body scanner embodiment has been discussed and it is only necessary to state briefly that the fan-shaped beam scans a layer and then the body is indexed axially by an amount substantially equal to the thickness of the beam. This process is repeated until all of the layers in the body of interest have been scanned and the x-ray intensity data has been taken.

The whole body scanner embodiment shown in FIGS. 21 and 22 does not use the feature of having the body surrounded by water. The method of gathering the x-ray intensity data with the encoder controlled system, nevertheless, applies.

Although many of the principles discussed above have been exemplified in terms of x-radiation examination apparatus, it will be appreciated by those versed in the art that the principles are applicable as well to other radiation examination equipment such as that which uses ultrasonic and gamma radiation.

We claim:

1. Apparatus for examining at least a portion of a body such as a breast with a scanned x-ray beam, comprising:
    scan arm means rotatable about a vertical axis that is disposed for being directed through the body portion that is to be examined,
    x-ray source means and x-ray detector means mounted on said scan arm means on opposite sides of said axis, said source means being operative to project an x-ray beam through a layer of said body portion toward said detector means,
    an x-ray permeable inner container having side wall means with upper edges defining a top opening and being disposed on said axis for containing the body portion and a fluid having x-ray absorption properties comparable to water, which fluid contacts and surrounds said body portion,
    an outer container having x-ray permeable side wall means surrounding the inner container and defining a space for water,
    means for rotating said outer container concurrently with said scan arm means,
    means for supporting a body in a position for said body portion to extend generally vertically into said inner container and to permit tissue adjacent said portion to be substantially contiguous with the upper edges of said inner container, and
    conduit means for communicating fluid to and from said containers.

2. The apparatus in claim 1 wherein said inner container is stationary.

3. The apparatus as in claim 1 wherein said conduit means is coupled to said container means in the bottom region thereof such that there will be an upward flow of said water in at least said inner container when fluid is being admitted to said container.

4. The apparatus as in claim 1 including means for assuring that said inner container may be filled with fluid sufficiently to contact said tissue adjacent said body portion, said means including means for intercepting fluid that overflows from said container and drain means coupled to said intercepting means.

5. The apparatus as in claim 1 including:
    a source of fluid coupled with said conduit means and flow control means in said conduit means between said source and said containers,
    controller means for selectively actuating said flow control means to enable and inhibit fluid flow, respectively, means for causing said controller means to cause said flow control means to enable fluid flow, and means responsive to said container means becoming partially filled to a predetermined level by causing said controller means to cause said flow control means to inhibit fluid flow.

6. The apparatus in claim 5 including:

means for causing said controller means to cause said flow control means to enable further fluid flow to said container means, and means responsive to said container means becoming filled by causing said controller means to cause said flow control means to inhibit fluid flow.

7. The apparatus in claim 6 wherein said controller means is constructed and arranged for responding further to said container becoming filled by controlling said flow control means to permit continuing fluid flow at a rate that is substantially smaller than the rate at which it permits fluid flow when filling to completion, whereby there will be a continuous overflow of fluid from said container to assure that it is filled to the edges thereof during an x-ray scan.

8. The apparatus in claim 6 including:

a storage tank for fluid and pump means coupled to said storage tank and said flow control means, means responsive to said flow control means being activated to effect partial filling of said container means by causing said pump means to deliver fluid to said container at one rate, and means responsive to said controller means enabling further filling of said container by causing said pump means to deliver fluid at another rate which is slower than said one rate.

9. The apparatus as in claim 1 including:

a storage tank for fluid that is to be used in said containers, means for coupling said storage tank to a source of fluid, means for controlling the flow of fluid to said tank periodically so that fluid may be collected therein in substantially the amount required for examination of the next patient, pump means having an inlet coupled to said tank and having an outlet, flow control means coupling said pump outlet to said conduit means, and means for conditioning water that is delivered to said container.

10. The apparatus in claim 9 including:

vacuum pump means having an inlet and an outlet and valve means interposed between said inlet and said storage tank means.

11. The apparatus in claim 1 including:

means for collimating the x-ray beam from said source to a fan-shaped beam that diverges in the direction toward the containers and said x-ray detector means, said fan-shaped beam being relatively thin in the axial direction, said detector means comprising an array of detectors arranged for intercepting substantially the width of said diverging beam, said outer rotating container means having sufficient width to present fluid in the path of at least that part of said fan-shaped x-ray beam which is intercepted by said detector means such that there will be substantially uniform x-ray absorption across said fan-shaped beam.

12. The apparatus in claim 11 wherein said outer container is rectangular in cross section.

13. The apparatus in claim 11 wherein said outer container has a cross section comparable to the shape of said diverging beam so that it effects uniform x-ray absorption across the beam.

14. The apparatus in claim 11 including:

first support means for supporting said inner container stationarily in said rotational axis, revolvable means mounted on said first support means for revolving about said axis, said outer fluid container being mounted on said revolvable means for turning at a fixed level.

15. The apparatus in claim 14 including:

translatable means on which said scan arm means is mounted for rotation, said means being axially translatable to cause the x-ray beam to be directed through different layers of said body portion, means for coupling said rotatable scan arm means in driving relation with said revolvable outer container support means, said means for coupling being constructed and arranged for enabling axial movement of said scan arm means relative to said revolvable means and said outer container.

* * * * *